(12) United States Patent
Van Lierop et al.

(10) Patent No.: US 12,066,620 B2
(45) Date of Patent: Aug. 20, 2024

(54) MEMS MIRROR FOR OCT PROBE AND METHOD OF MANUFACTURING SUCH MEMS MIRROR

(71) Applicant: Scinvivo B.V., Eindhoven (NL)

(72) Inventors: Hendrikus Wilhelmus Leonardus Antonius Maria Van Lierop, Weert (NL); Maaike De Jong, Eindhoven (NL); Geert Claassen, Velp (NL)

(73) Assignee: Scinvivo B.V., Eindhoven (NL)

( * ) Notice: Subject to any disclaimer, the term of this patent is extended or adjusted under 35 U.S.C. 154(b) by 854 days.

(21) Appl. No.: 16/979,083

(22) PCT Filed: Mar. 8, 2019

(86) PCT No.: PCT/NL2019/050154
§ 371 (c)(1),
(2) Date: Sep. 8, 2020

(87) PCT Pub. No.: WO2019/172767
PCT Pub. Date: Sep. 12, 2019

(65) Prior Publication Data
US 2021/0055543 A1    Feb. 25, 2021

(30) Foreign Application Priority Data

Mar. 9, 2018  (NL) .................................. 2020564

(51) Int. Cl.
*G02B 26/08* (2006.01)
*A61B 5/00* (2006.01)
(Continued)

(52) U.S. Cl.
CPC ........ *G02B 26/0841* (2013.01); *A61B 5/0066* (2013.01); *G01B 9/0205* (2013.01);
(Continued)

(58) Field of Classification Search
CPC ............ G02B 26/0841; G01B 9/02091; A61B 2562/0242; A61B 2562/028
See application file for complete search history.

(56) References Cited

U.S. PATENT DOCUMENTS

| 8,274,722 B2* | 9/2012 | Moidu | G02B 26/0841 359/224.1 |
| 2003/0019832 A1* | 1/2003 | Conant | G02B 26/0841 216/2 |

(Continued)

FOREIGN PATENT DOCUMENTS

| EP | 1180493 A2 | 2/2002 |
| WO | 2009023635 A1 | 2/2009 |

(Continued)

OTHER PUBLICATIONS

D. Hah et al, "Theory and Experiments of Angular Vertical Comb-Drive Actuators for Scanning Micromirrors", IEEE Journal of Selected Topics in Quantum Electronics, vol. 10, No. 3, pp. 505-513, Jun. 2004 (Year: 2004).*

(Continued)

*Primary Examiner* — Joel Lamprecht
*Assistant Examiner* — Nyrobi Celestine
(74) *Attorney, Agent, or Firm* — Banner & Witcoff, Ltd.

(57) ABSTRACT

A forward looking MEMS based OCT probe (50) is provided that comprises an elongate probe housing (51) having at a first end a probe interface (54) for an optic fibre (56), and at a second opposite end a viewing window (58). The probe housing accommodates a MEMS mirror (10) for sweeping a light beam (60) through the viewing window and for reflecting light received through the viewing window towards the probe interface, wherein a rotation axis (18) of the MEMS mirror extends transverse to a longitudinal axis (62) defined by the probe housing. The MEMS mirror (10) has a stator (12), a rotor (14), and an actuator (16) with at least one pair (Continued)

of mutually interdigitated comb elements including at least a first comb element fixed to the stator defining a reference plane and at least a second comb element fixed to the rotor and that is further coupled at mutually opposite sides via a respective torsion beam (20A, 20B) to the stator. The rotor has a rotor body (14RB) and a rotor support (14RS), fixed at a first face of the rotor body, that keeps the rotor body at a distance from the stator within said rotation range, the rotor body having a mirror surface (14MS) at a second face opposite the first face, the MEMS mirror comprising the stator (12) and the rotor support (14RS) at mutually opposite sides of the reference plane (RP).

20 Claims, 29 Drawing Sheets

(51) Int. Cl.
*G01B 9/02* (2022.01)
*G01B 9/02091* (2022.01)

(52) U.S. Cl.
CPC .. *G01B 9/02091* (2013.01); *A61B 2562/0242* (2013.01); *A61B 2562/028* (2013.01); *A61B 2562/12* (2013.01)

(56) References Cited

U.S. PATENT DOCUMENTS

| | | | | |
|---|---|---|---|---|
| 2006/0082250 A1* | 4/2006 | Ko | ............ | H02N 1/008 310/309 |
| 2007/0018065 A1 | 1/2007 | Denatale et al. | | |
| 2007/0026614 A1* | 2/2007 | Choo | ............ | G02B 26/0841 438/275 |
| 2007/0053035 A1* | 3/2007 | Cho | ............ | G02B 26/101 359/224.1 |
| 2007/0216986 A1* | 9/2007 | Huber | ............ | G02B 26/0841 359/245 |
| 2008/0197748 A1* | 8/2008 | Naftali | ............ | B81B 3/0043 310/309 |
| 2009/0153932 A1* | 6/2009 | Davis | ............ | G02B 26/0841 359/199.1 |
| 2009/0180169 A1 | 7/2009 | Moidu et al. | | |
| 2010/0103494 A1* | 4/2010 | Moidu | ............ | G02B 26/0841 438/666 |
| 2010/0172612 A1* | 7/2010 | Moidu | ............ | B81B 3/0062 359/199.2 |
| 2012/0218613 A1* | 8/2012 | Maruyama | ............ | G02B 26/0841 359/200.6 |
| 2013/0194654 A1* | 8/2013 | Moidu | ............ | G02B 26/0841 359/291 |
| 2014/0376069 A1 | 12/2014 | Reinmuth | | |
| 2015/0002916 A1* | 1/2015 | Sourani | ............ | G02B 7/1821 359/199.2 |
| 2017/0199374 A1* | 7/2017 | Miller | ............ | H01S 5/06 |

FOREIGN PATENT DOCUMENTS

| | | |
|---|---|---|
| WO | 2009044331 A2 | 4/2009 |
| WO | 2010086861 A1 | 8/2010 |

OTHER PUBLICATIONS

D. Hah et al, "Low-Voltage, Large-Scan Angle MEMS Analog Micromirror Arrays With Hidden Vertical Comb-Drive Actuators", Journal of Microelectromechanical Systems, vol. 13, No. 2, pp. 279-289, Apr. 2004 (Year: 2004).*
J. Kim et al, "Monolithic 2-D Scanning Mirror Using Self-Aligned Angular Vertical Comb Drives", IEEE Photonics Technology Letters , vol. 17, No. 11, pp. 2307-2309, Nov. 2005 (Year: 2005).*
D. Dao et al, "Polymer-MEMS torsion mirror with large rotation angle and low driving voltage", International Conference on Optical MEMS and Nanophotonics, pp. 27-28, Dec. 2010 (Year: 2010).*
Y. Liu et al, "Large size MEMS scanning mirror with vertical comb drive for tunable optical filter", Optics and Lasers in Engineering, vol. 51, pp. 54-60, Aug. 2012 (Year: 2012).*
T. Izawa et al, "Scanning Micro-Mirror with an Electrostatic Spring for Compensation of Hard-Spring Nonlinearity", Micromachines, vol. 8, pp. 1-13, Aug. 2017 (Year: 2017).*
J. Cheng et al, "A mems variable optical attenuator based on a vertical comb drive with self-elevated stators", Sensors and Actuators A: Physical, vol. 271, pp. 398-408, Mar. 2018 (Year: 2018).*
Jul. 12, 2019, International Search Report and Written Opinion, PCT/NL2019/050154.

* cited by examiner

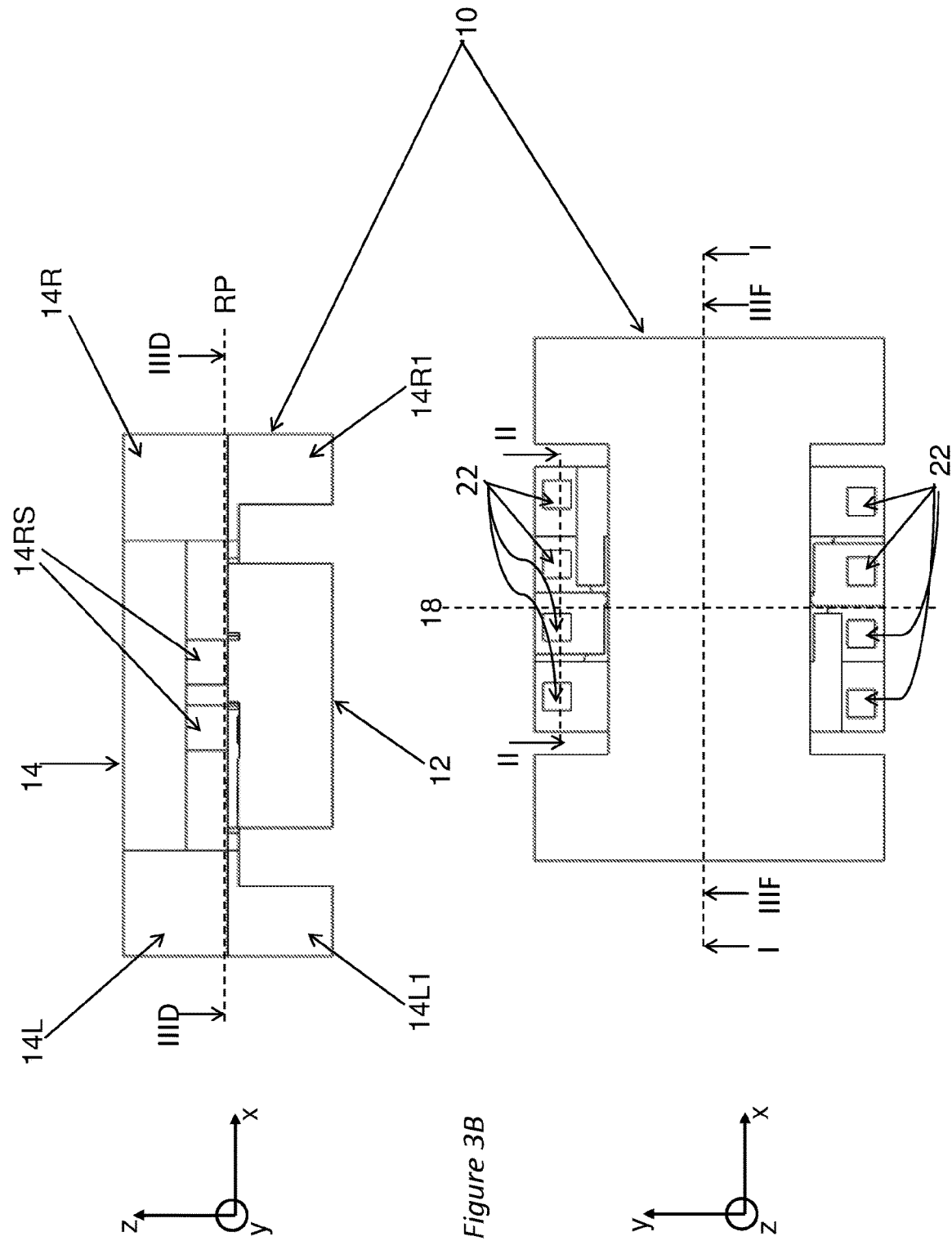

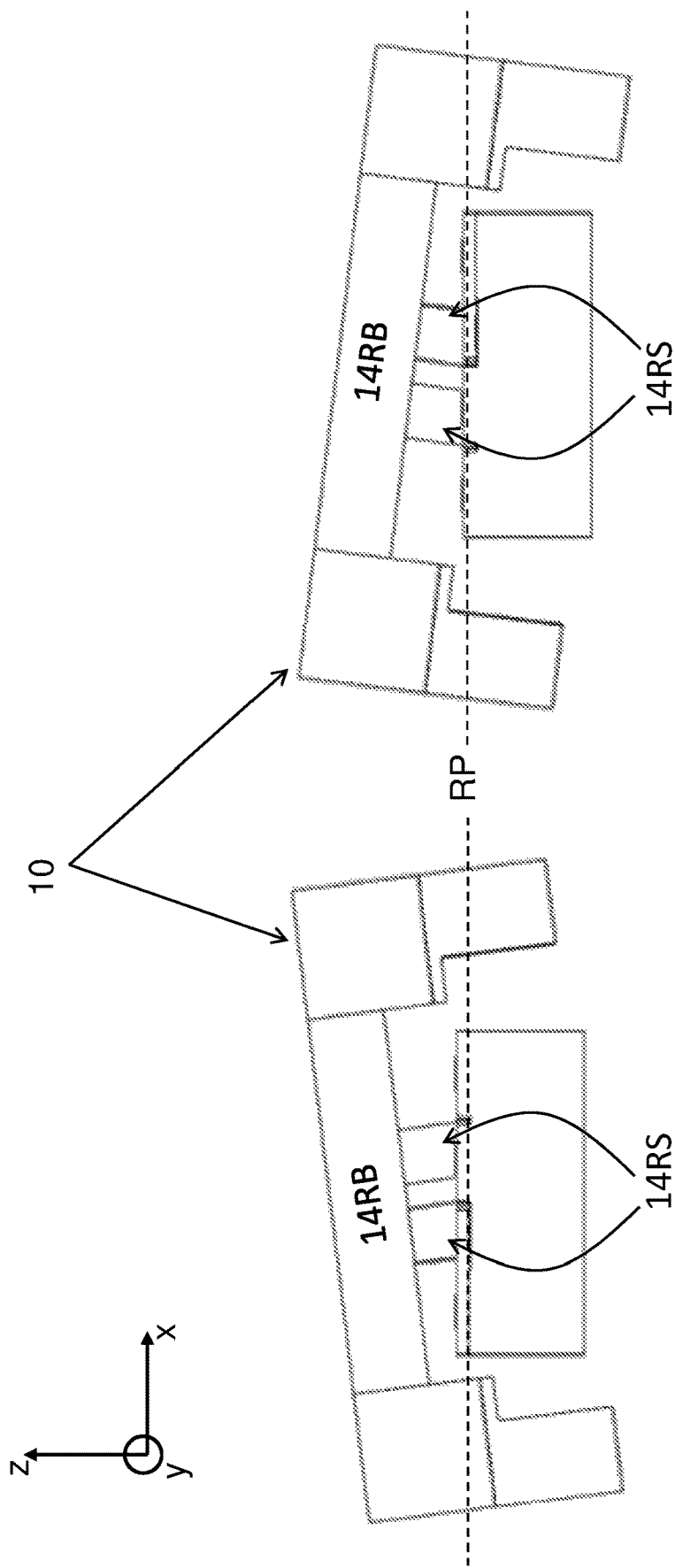

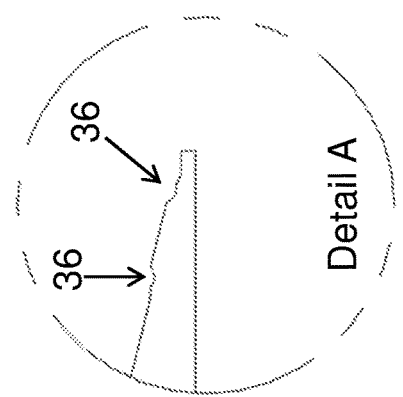
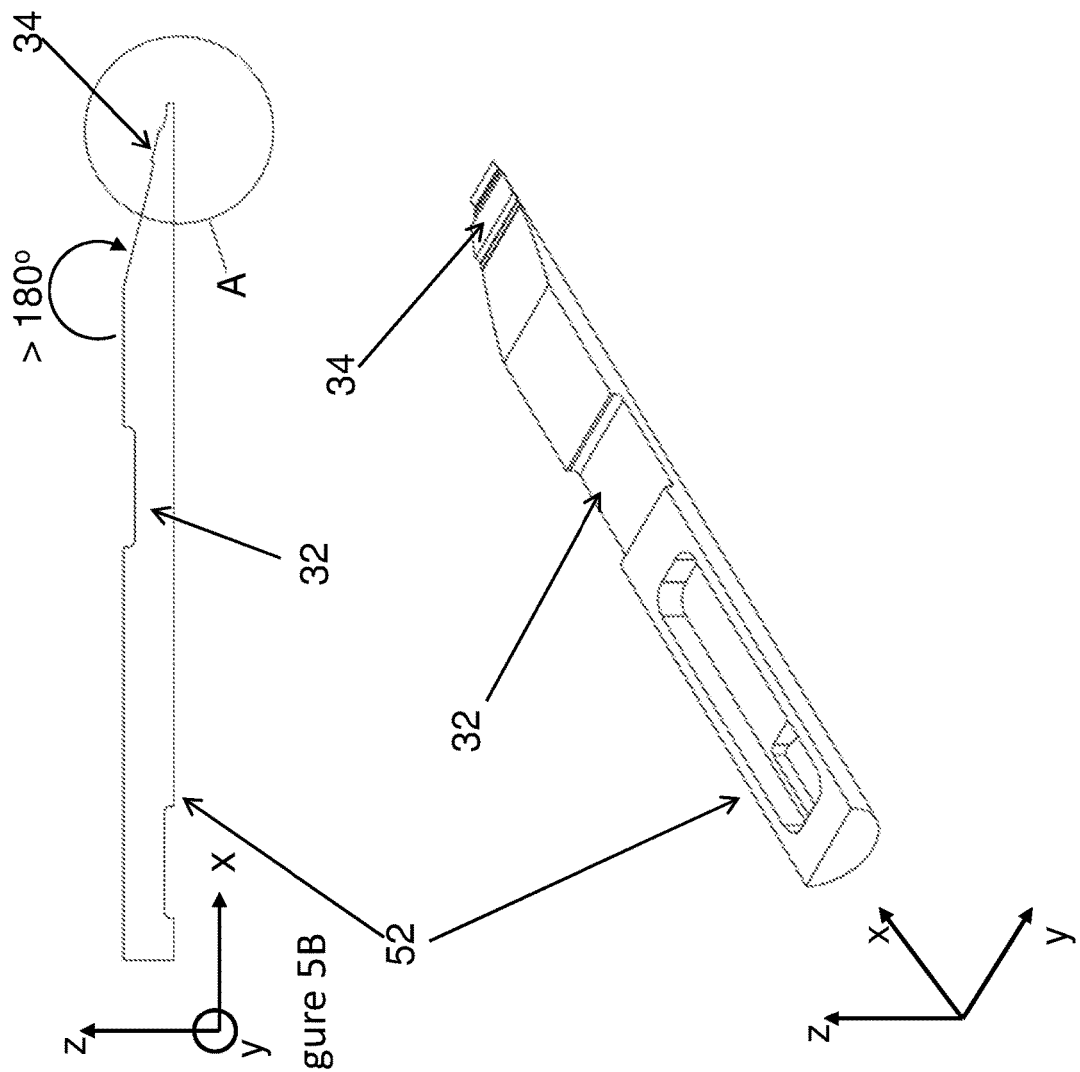

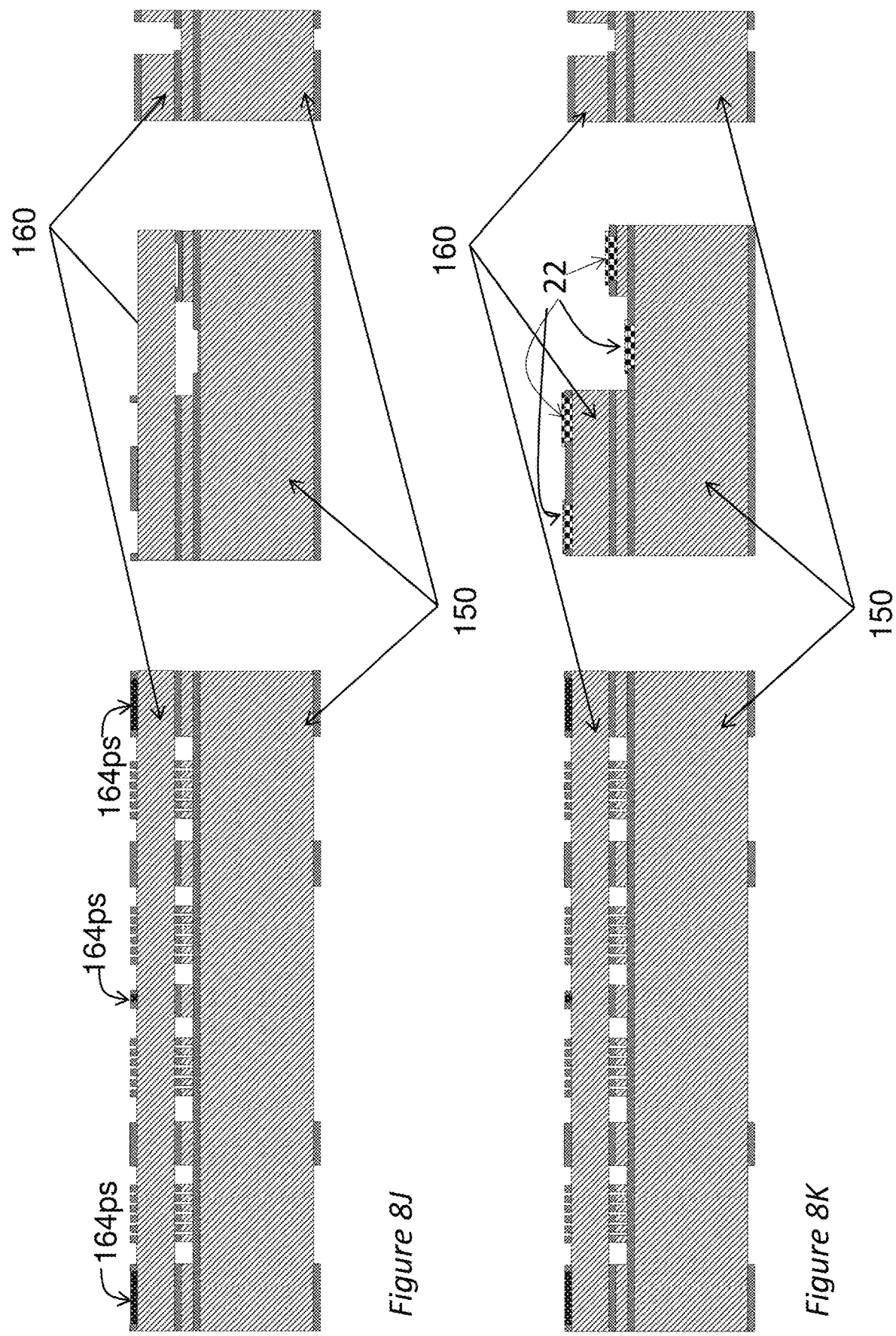

MEMS MIRROR FOR OCT PROBE AND METHOD OF MANUFACTURING SUCH MEMS MIRROR

CROSS-REFERENCE TO RELATED APPLICATIONS

This application is a U.S. National Stage application under 35 U.S.C. § 371 of International Application PCT/NL2019/050154 (published as WO 2019/172767 A1), filed Mar. 8, 2019, which claims the benefit of priority to Application NL 2020564, filed Mar. 9, 2018. Benefit of the filing date of these prior applications is hereby claimed. Each of these prior applications is hereby incorporated by reference in its entirety.

FIELD OF THE INVENTION

The invention relates to forward looking optical coherence tomography endoscopic probes for biological in vivo tissue imaging, based on MEMS scanner technology.

BACKGROUND OF THE INVENTION

Optical coherence tomography (OCT) enables real-time, high resolution, in depth imaging of tissue. OCT can be used for minimal invasive disease diagnosis optical biopsies, image guided surgery, and photodynamic therapy.

OCT is an imaging technology which, analogous to ultrasound, provides in-depth cross-sectional images of the examined tissue. In comparison with ultrasound, OCT makes use of light instead of soundwaves. The resolution of OCT is higher than that of ultrasound (in the micrometre range), and the penetration depth is lower than for ultrasound (in the millimetre range). Analogous to ultrasound, a cross-sectional scan at one point (pixel) is called an A-scan, while a 2D cross sectional scan over a line, so multiple A scans in a row, is called a B-scan.

Optical coherence tomography is based on a Michelson interferometer, FIG. 1 shows an example of a Fourier domain OCT system. With Fourier domain OCT systems a beam from a light source 200 is split into two arms at a beam splitter 202, a reference arm 204 and a sample arm 206. A piece of tissue T is placed at the end of the sample arm. The light beam in the reference arm reflects back from the mirror placed at the end of the reference arm 210, the light beam in the sample arm reflects from the different layers in the tissue. These beams are combined again at the beam splitter 202. This results in an interference signal DS, which is detected 212 and translated into an image 214 after processing 216. The acquired interference signal is the integrated spectrum of a broad spectrum light source. All fringes are superimposed in one signal, and the frequency of the different fringes corresponds with the different path lengths. Via Fourier transform of the detected signal the sample reflectance can be obtained as a function of depth, for all depths at once.

The sample arm may comprise an elongate catheter or probe that has a probe interface at a first end to be coupled to a beam guide, such as an optic fibre and at a second opposite end a viewing window. A MEMS mirror may be accommodated in the probe for sweeping a light beam through the viewing window and for reflecting light received through the viewing window towards the probe interface. The probe interface may comprise one or more elements, such as a GRIN lens and a static mirror, to properly redirect the beam to be reflected by the MEMS-mirror. An example thereof is disclosed by Kim et al. in "Two-axis magnetically-driven MEMS scanning catheter for endoscopic high-speed optical coherence tomography", OPTICS EXPRESS, Vol. 15, No. 26, 24 Dec. 2007.

Other examples of a construction of an OCT-probe are provided by Tearney et al. in "Scanning single-mode fiber optic catheter-endoscope for optical coherence tomography", Apr. 1, 1996/Vol. 21, No. 7/OPTICS LETTERS. Tearney et al. describe a catheter-endoscope having at its distal end a gradient-index lens with a microprism to emit and collect a single spatial-mode optical beam with specific focusing characteristics. Also Jung et al. reports use of a GRIN lens in combination with a prism in this context. See "Numerical analysis of gradient index lens-based optical coherence tomography imaging probes", Journal of Biomedical Optics 15(6), 066027 (November/December 2010).

OCT is a microscopic imaging technology, which means that it can be used to examine a small area of tissue at one time. Another name to describe OCT is 'optical biopsy' as it provides for a method to obtain information comparable to that obtainable with a real biopsy, however while avoiding an invasive procedure.

OCT is already state of the art in ophthalmology, and more application areas are being developed. Early detection of cancerous tissue is one of the main goals in the medical world, and OCT is a useful tool for early cancer diagnosis, as it enables the physician to look inside the tissue with a high resolution.

One example of a medical area in which there is an unfulfilled need for better diagnostic technologies is urology. Current diagnostic techniques for bladder cancer have their limitations, resulting in large amounts of false positives and false negatives. With OCT, a cross-sectional image of the bladder wall can be provided to the urologist. Based on these OCT-images the urologist can make a more accurate diagnosis. To be able to use OCT inside the human body, it is necessary to put the technology in a small catheter that is watertight and can be sterilized.

Two types of catheters that are already developed for in vivo tissue imaging can be discerned: 1) forward looking catheters; and 2) sideway looking catheters. The sideway looking catheters are ideal for the imaging of tube-shaped organs, as the working distance stays constant and with an automatic pull-back a 3D image of the full tubular organ can be formed.

It is well known in the art that there is a need for forward looking endoscopic OCT catheters for in vivo use. Forward looking catheters are necessary to image hollow organs. Hollow organs cannot be imaged in the same way as tubular organs, as they are irregularly shaped and the working distance will change continuously. An automatic pull-back to form a 3D image in one go is not possible for these hollow organs. Examples of hollow organs are: bladder, uterus, stomach, and lungs.

Forward looking OCT catheters are designed for use in an endoscopic device with a camera. In that assembly the OCT catheter is directed to the same plane of view as the camera. Apart from hollow shaped organs, other interesting application areas for forward looking catheters are the vocal cords and the inner ear.

Forward looking OCT catheters are designed in two different ways: 1) based on a sweeping fibre inside the catheter; and 2) based on a microelectromechanical system (MEMS) mirror laser scanner. To be able to image a large field of view, a MEMS mirror based laser scanner module is necessary. This 1D or 2D scanner will steer the light to the tissue, collect the back reflected light from the tissue, and guide it back into the optical fibre.

MEMS are a combination of micro-optics, microelectronics, and micromechanics. With high-tech semi-conductor processes a device can be built layer by layer on microscopic scale. MEMS are very beneficial for use in biomedical imaging applications as they are very small, can operate at high speed to enable real time imaging, are easy to integrate with the rest of the optical system, are cheap to manufacture, and have a low power consumption.

To develop a miniature laser scanning module, a MEMS mirror can be used. Four different MEMS actuation methods can be distinguished: 1) electrostatic; 2) electromagnetic; 3) piezoelectric; and 4) electrothermal. Of these four actuation methods, only electrostatic MEMS and electrothermal MEMS are currently suitable for in vivo imaging. Drawbacks of electromagnetically actuated mirrors are that they need a high current, and the fact that they require external magnets or coils, which limits a further miniaturization. Drawbacks of piezoelectric mirrors are that they have hysteresis effects and require additional manufacturing steps. Electrostatic mirrors have the benefit that they can reach high resonant frequencies, when compared to electrothermal actuators, which makes them ideal for scanning applications. A downside is that the drive voltage is high.

The light that enters the sample arm within the OCT system can be reflected by a (MEMS) scanner, onto a target tissue sample for imaging. The MEMS scanner moves the light beam in the lateral direction, enabling 2D or 3D scanning. The light in the sample arm can pass through a lens assembly before it reaches the sample. The lens can be positioned between the MEMS scanner and the sample ("post-scan optics"), or the MEMS scanner can be positioned between the lens assembly and the sample ("pre-scan optics"), or lenses can be used both before and after the MEMS mirror The scanner and lens assembly can be placed inside a probe, that can be used to image inside a person if the probe is protected by a catheter sleeve. This catheter then has to fit inside the working channel of an endoscope. Alternatively, the probe can be placed in the endoscope self.

The MEMS scanner may comprise a reflective surface, for example suspended by torsion beams, rotatable around one or two axes which are located in a single operating plane, to guide light towards the tissue sample. The scanning reflector can be a vertical comb drive actuated microscanner. The mirror may be of silicon, coated with a metal, e.g. gold, silver, or aluminium.

The lens assembly may contain a gradient-index lens. The axial resolution of the system is determined fully by the wavelength range of the light source, for example a swept source laser. The lateral resolution is determined by the optical assembly inside the probe and the MEMS scanner.

SUMMARY OF THE INVENTION

It is a first object of the present invention to provide a MEMS mirror that is suitable for use in an optical coherence tomography endoscopic probe.

It is a second object of the present invention to provide a forward looking optical coherence tomography endoscopic probe of relatively small dimensions while having a relatively large lateral scanning angle, including such a MEMS-mirror.

It is a third object of the invention to provide a method of manufacturing such a forward looking optical coherence tomography endoscopic probe.

According to the first object a MEMS mirror is provided as disclosed herein.

A MEMS mirror as disclosed herein has a stator, a rotor, and an actuator. The actuator has at least one pair of mutually interdigitated comb elements including at least a first comb element and a second comb element. The first comb element is fixed to the stator and defines a reference plane. The reference plane is parallel to the top- and bottom surfaces of the comb element, when the mirror is at rest and at its neutral position. The reference plane is located between the top and bottom surfaces of the comb element. The second comb element is fixed to the rotor and the rotor is further coupled at mutually opposite sides via a respective torsion beam to the stator. These torsion beams, one at each end extend along a rotation axis in the reference plane to allow the actuator, when driven with an AC signal to rotate the rotor within a rotation range relative to the stator along the rotation axis. Therewith the second comb element sweeps back and forth through the reference plane. In the absence of a drive voltage the second comb element typically is also oriented in the reference plane.

The rotor has a rotor body and a rotor support, fixed at a first face of the rotor body that keeps the rotor body at a distance from the stator within a rotation range. The rotor body has a mirror surface at a second face opposite the first face. The MEMS mirror comprises the stator and the rotor support at mutually opposite sides of the reference plane.

The construction of the MEMS mirror renders it possible to increase a surface area of rotor body and therewith the mirror surface, without being restricted by the surface area of the stator. This makes it possible to provide a relatively large mirror surface area in a forward looking MEMS based optical coherence tomography probe with relatively narrow cross-sectional dimensions. In particular this renders it possible that a size of the mirror surface in a direction transverse to the rotation axis is at least 90% of a size of the stator in that direction. In a practical example the size of the mirror surface in the transverse direction to the rotation axis is for example at most 200 micrometer smaller than a size of the stator in that direction. It is noted that a fill factor above 90% can be accomplished in conventional MEMS-mirror constructions when using through-silicon-via (TSV) technology. This technology is however unattractive as it requires a high temperature to electrically connect the MEMS-mirror to other elements in the probe, and as it requires additional processing steps to create and isolate the vias. The construction of a MEMS-mirror as disclosed herein allows other electrical connection methods, such as connection through wire-bond pads.

A construction of a MEMS-mirror as disclosed herein even allows a further increase of the mirror surface in the direction transverse to the rotation axis. For example, the size of the mirror surface in the transverse direction is at least equal to a size of the stator in that direction. For example in an embodiment the rotor body has peripheral portions that extend beyond the stator in the transverse direction. Although this does not result in a further increase of the fill factor, as it is now the rotor with the mirror surface that defines the footprint, at least in the transverse direction, this is favourable in that it results in an increased mirror surface, and a decrease of the resonance frequency of the mirror. Driving the mirror at its resonance frequency enables a low power operation and a relatively low resonance frequency is favourable for a high lateral resolution with which tissue can be imaged. An even further reduction of the resonance frequency without further increasing the footprint is possible in an embodiment wherein the peripheral portions have an extension portion that extends at a distance along a side face of the stator.

In an embodiment the actuator comprises at least one further pair of mutually intercligitated comb elements in said actuator layer including at least a third comb element fixed to the stator and a fourth comb element fixed to a peripheral portion of the rotor body. Therewith it is made possible to drive the MEMS-mirror with a lower drive voltage than would be the case in the absence of the further pair. Also, the extra capacitance provided by the further pair enables a more accurate detection of the zero crossing, i.e. the point in time where the combs of the rotor traverse the reference plane.

In an embodiment the torsion beams have a T-shaped cross-section in a plane transverse to the rotation axis. Torsion beams with this cross-section have a relatively low stiffness in the direction of rotation, which is favourable for a low resonance frequency, but provide for a high stiffness in other directions to prevent (rotational) movement in those directions.

The MEMS mirror can be used to manufacture a forward imaging Optical Coherence Tomography (OCT) probe as disclosed herein. A probe as disclosed herein comprises an elongate probe housing that has a probe interface for an optic fiber at a first end and a viewing window at an opposite end. In this connection it is noted that the viewing window is the aperture at the opposite end available to allow light to exit and to enter the probe housing. Preferably a solid transparent element is provided that avoids that fluids can enter the housing. However, such element does not necessarily coincide with the viewing window.

The probe housing accommodates a MEMS mirror as disclosed herein for sweeping a light beam through the viewing window and for reflecting light received through the viewing window towards the probe interface. The rotation axis of the MEMS mirror extends transverse to a longitudinal axis of the probe housing, corresponding to the longitudinal direction from the first end to the second end.

In an embodiment the housing of the probe further accommodates a driver having an output to provide a drive signal to the actuator. The driver integrated in the housing enables a more accurate control as influences of noise on the feedback signal are substantially smaller than would be the case if the driver is located outside the probe.

In an embodiment the driver further comprises a feedback input to receive a feedback signal indicative for a rotational state of the rotor. Furthermore, therein the driver is configured to provide a drive signal to the actuator based on the feedback signal. The feedback signal enables a reliable tracking of the actual rotational state of the MEMS-mirror. The feedback signal can be any signal that is indicative of the rotational state of the MEMS-mirror. In a preferred embodiment the zero crossing (synchronisation, or trigger) signal is chosen as the feedback signal as this can be obtained in a relatively simple manner, and provides sufficient information about the rotational state (amplitude) and rotational direction of the mirror. An external control signal may be used to start or interrupt operation or to correct the phase.

The driver typically includes a voltage controlled oscillator (VCO) to deliver the AC-drive signal for the MEMS-mirror. Typically further a phase locked loop (PLL) is included. In an initial stage the drive signal may be provided in an open-loop mode until it is detected that the MEMS-mirror is resonating. Subsequently, control may be continued in a closed loop mode, wherein the PLL controls the VCO to minimize a difference in the phase of the mirror as indicated by the feedback signal and the phase of the VCO.

In a resonance mode the MEMS-mirror for example has a resonance frequency in the range of 200 Hz to 4000 Hz.

In an embodiment the comb elements include a first and a second, mutually insulated, comb layer of an electrically conducting material, wherein the first comb layer is arranged at a side of the reference plane and faces the mirror surface, and the second comb layer faces away from the mirror surface. In this embodiment the first and the second comb layer form a first and a second electric pole in each of the comb elements. The first electric poles of each of the comb elements of the rotor are electrically interconnected with each other and are electrically connected to the output of the driver. At least one of a first and a second electric pole of each of left and right comb elements of the stator are coupled to a respective feedback input of the driver, wherein the left and right comb elements of the stator are arranged at mutually opposite sides of the rotation axis.

This embodiment of the MEMS-mirror, connected in this manner to the driver makes it possible not only to determine the point in time that zero-crossing takes place, but also enables a determination of the movement direction of the mirror.

In an embodiment the probe in its longitudinal direction, from its first end to its second end, contains one or more of a spacer (optional), a GRIN lens bound by tilted faces with respect to said longitudinal direction (optional), a prism (optional), and further the MEMS mirror and the viewing window. The one or more elements selected from a spacer, a GRIN lens and a prism provide for an optical path, that directs the beam received from an single mode fiber (or other optical channel) to the MEMS-mirror and to direct the light received via the viewing window towards the optical channel. A GRIN lens is a preferred element for this purpose. As an alternative a ball lens can be used, but the latter requires a larger volume.

In an embodiment, the probe housing accommodates a carrier having a main portion extending in a direction that substantially coincides with a longitudinal direction of the housing and an end portion facing the viewing window. In this embodiment the main portion carries the driver and the end portion carries the MEMS mirror. The surface of an end portion of the carrier at a side carrying the MEMS mirror is tilted with respect to the longitudinal direction. In particular an angle defined between the surface end portion carrying the MEMS-mirror and the adjoining surface of the main portion of the carrier defines an angle greater than 180 degrees. Therewith the MEMS-mirror positioned and oriented in a manner that enables forward looking.

In this embodiment, when combined with a MEMS-mirror having peripheral portions that have an extension portion extending at a distance along a side face of the stator the end portion of the carrier may be provided with recesses facing the peripheral portions, or may be provided with an elevated pedestal to place the stator part of the MEMS on. Therewith it is achieved that the carrier properly supports the MEMS-mirror while avoiding that it restricts movements of the mirror.

A forward looking MEMS based OCT system is further provided that may include any of the embodiments of the OCT probe as defined above, and that further includes:
   a coherent light source configured a to generate a coherent light beam;
   a beam splitter/merger to split the coherent light beam into a reference beam and a sense beam;

a reference unit to receive and reflect the reference beam; and wherein the probe interface of the OCT probe is to receive the sense beam and the beam splitter/merger is to receive the light reflected from the tissue and received through the viewing window and reflected by the resonant mirror, to receive the reflected reference beam and to merge the beams received from the reference unit and the probe;

a detector to generate a detection signal indicative for the merged beams;

a processing unit to process the detection signal.

According to the second object a method of manufacturing a forward looking MEMS based optical coherence tomography probe is provided.

In an embodiment the MEMS mirror is manufactured by starting with 3 silicon wafers, of which two (the base wafer and the comb wafer) can be a SOI wafer, having a 1 µm thick silicon device layer. The two wafers with the silicon device layer will form the insulated device layers of the MEMS. At first, in the base wafer the structure for the comb drives, torsion beams, and holes for the bond pads (at least three on each side, four in this embodiment) will be etched. Next, the comb wafer will be connected to the base wafer via fusion bonding (or a similar technique), for which it is important that the wafers are electrically insulated via a siliconoxide layer. The comb wafer will be ground to a very thin layer, in which the same comb structure, and a different torsion beam structure will be etched and also holes for the bond pads will be etched. The bond pad holes will be filled with a metal or alloy, for example AlCu, to be able to make an electrical connection with the different device layers. The last wafer (the mirror wafer) will be etched and connected to the other two wafers via an eutectic bond, such that an electrical connection is enabled. Finally, the assembly is turned around such that the bottom structure can be etched. This is done last to provide more stability and rigidity during the earlier process steps. Alternatively, the manufacturing process can start with 2 silicon wafers of which one can be a DSOI wafer, having two 1 µm thick silicon device layers. The DSOI wafer with the silicon device layers will form the insulated device layers of the MEMS. However, using a DSOI wafer limits the freedom to pattern the bottom device layer differently compared to the top device layer.

In an embodiment the carrier parts are manufactured by 3D printing the structures with medical grade plastic. The carrier parts can have openings for main components of the probe, such as an inductor, the driver, and the MEMS. Also, the top carrier construction can be provided with a slot for the optical fiber. 3D printing allows for a rigid structure which can protect and align all components.

In an embodiment a catheter sleeve of a medically approved material can be pulled around the device to ensure the probe is watertight, can be sterilized, and can be used in vivo in humans.

The improvements of the forward looking MEMS based optical coherence tomography probe are in particular enabled by the incorporation therein of a MEMS-mirror as disclosed herein. It will be appreciated that an improved MEMS-mirror may also be applicable in other products and may be manufactured according to various embodiments as disclosed herein.

BRIEF DESCRIPTION OF THE DRAWINGS

These and other aspects of the invention are described in more detail with reference to the drawings. Therein:

FIG. 3B is a side view along the y-axis of the embodiment of FIG. 3A.

FIG. 3C is a top view along the z-axis of the embodiment of FIG. 3A.

FIG. 3E shows two rotational states of the MEMS mirror according to the same view as FIG. 3B.

FIGS. 5A, 5B and 5C schematically shows an embodiment of the carrier part of the housing of the probe. Therein FIG. 5A is a perspective view, FIG. 5B is a side view and FIG. 5C shows a detail according to A in FIG. 5B.

DETAILED DESCRIPTION

Figure 2:
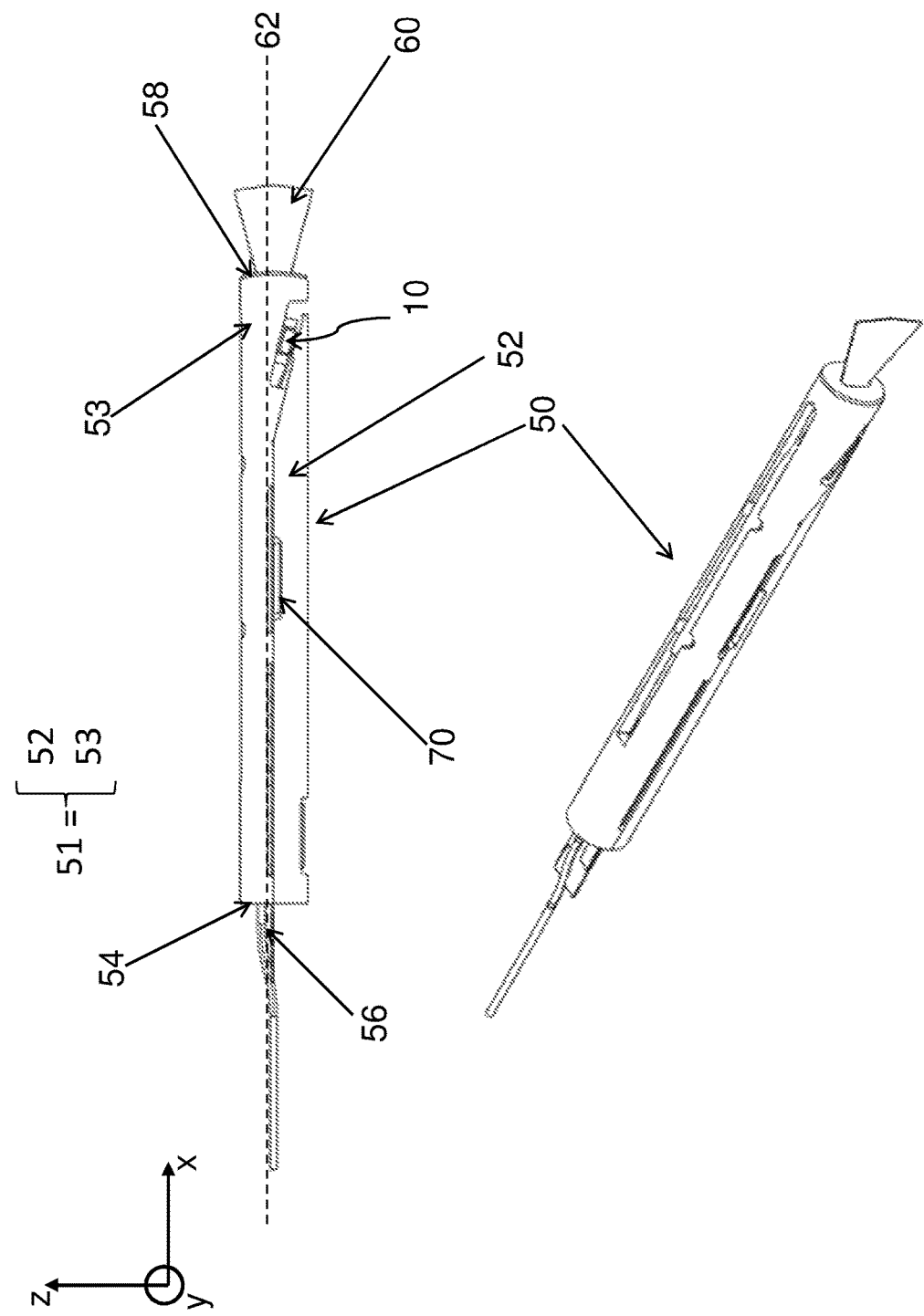
FIG. 2 schematically shows the an embodiment of the probe described in this invention, that is to be connected with the swept source OCT system.

Referring to FIG. 2, an embodiment of a forward looking MEMS based optical coherence tomography probe 50 as disclosed herein is pictured. The probe 50 comprises an elongated probe housing 51, consisting of a carrier part 52 and a top part 53, and having at a first end a probe interface 54 for an optic fibre 56. At a second end, opposite to the first end, the probe has a viewing window 58. The viewing window can be open or it can be closed off with a transparent solid, e.g. glass. Inside the probe housing 51 a MEMS mirror 10 is arranged, which, in operation, sweeps a light beam 60 through the viewing window onto a sample, for example tissue in a hollow organ of the human body. The MEMS mirror also guides light reflected from the sample and received through the viewing window back into the optic fibre 56 via the probe interface 54.

The MEMS mirror 10, an embodiment of which is shown in FIG. 3A-3I has a mirror surface 14MS on a rotor body 14RB with a rotation axis 18 that is arranged transverse to a longitudinal axis 62 that extends in a direction from the first to the second end of the described probe housing 51, as shown in FIG. 2. Therein FIG. 3A-3H illustrate the embodiment of the MEMS mirror in various views and cross-sections as indicated above.

Figure 3A:
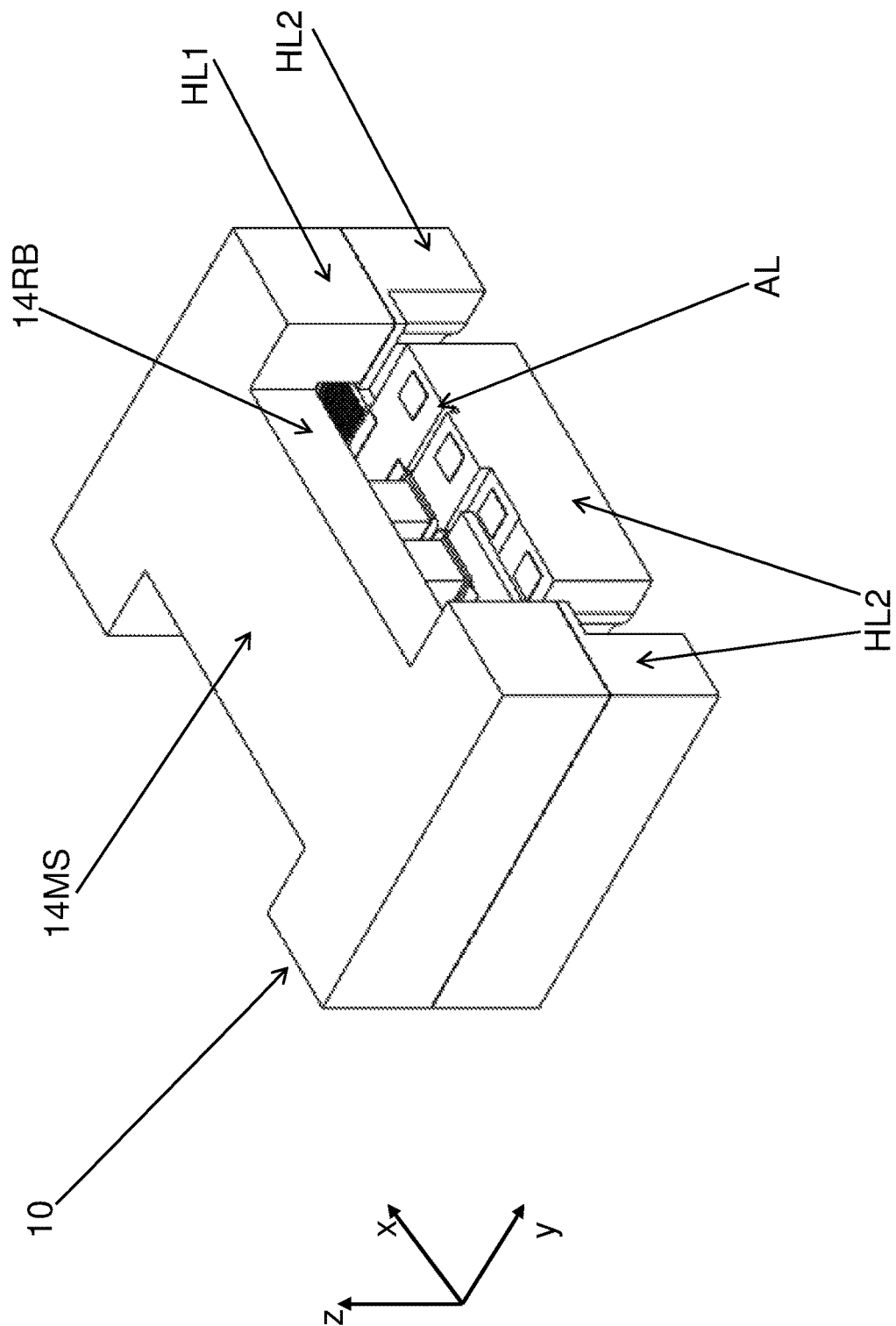
FIG. 3A is a perspective view schematically showing an embodiment of a MEMS mirror as disclosed herein.
Figure 3D:
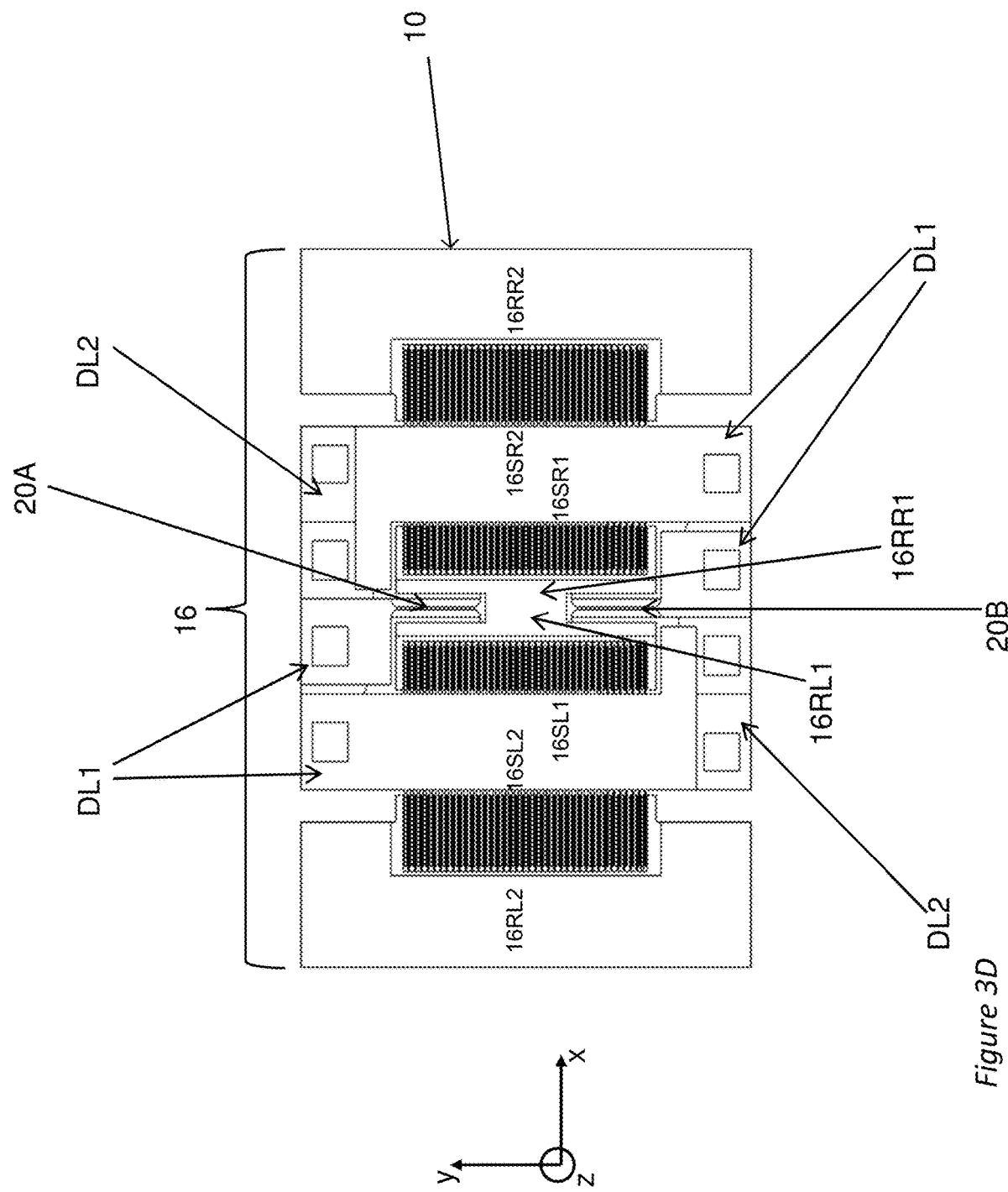
FIG. 3D is a cross-section according to IIID-IIID in FIG. 3B.
Figure 3F:
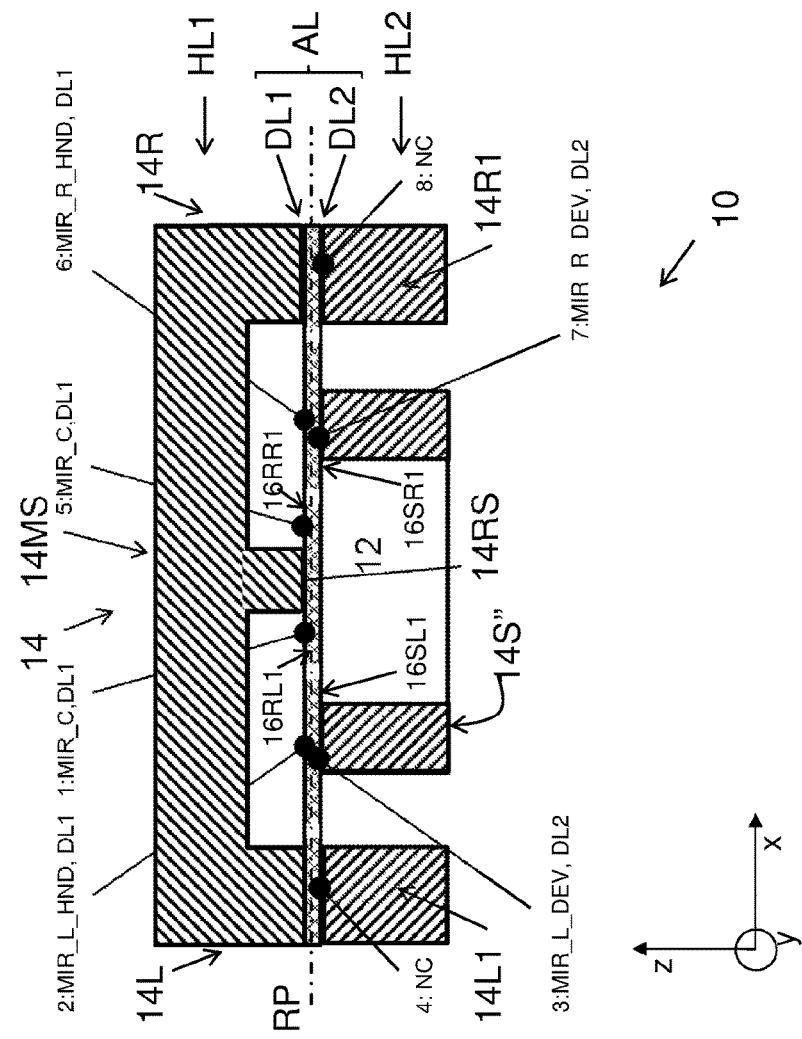
FIG. 3F is a cross-section according to IIIF-IIIF in FIG. 3C.
Figure 3G:
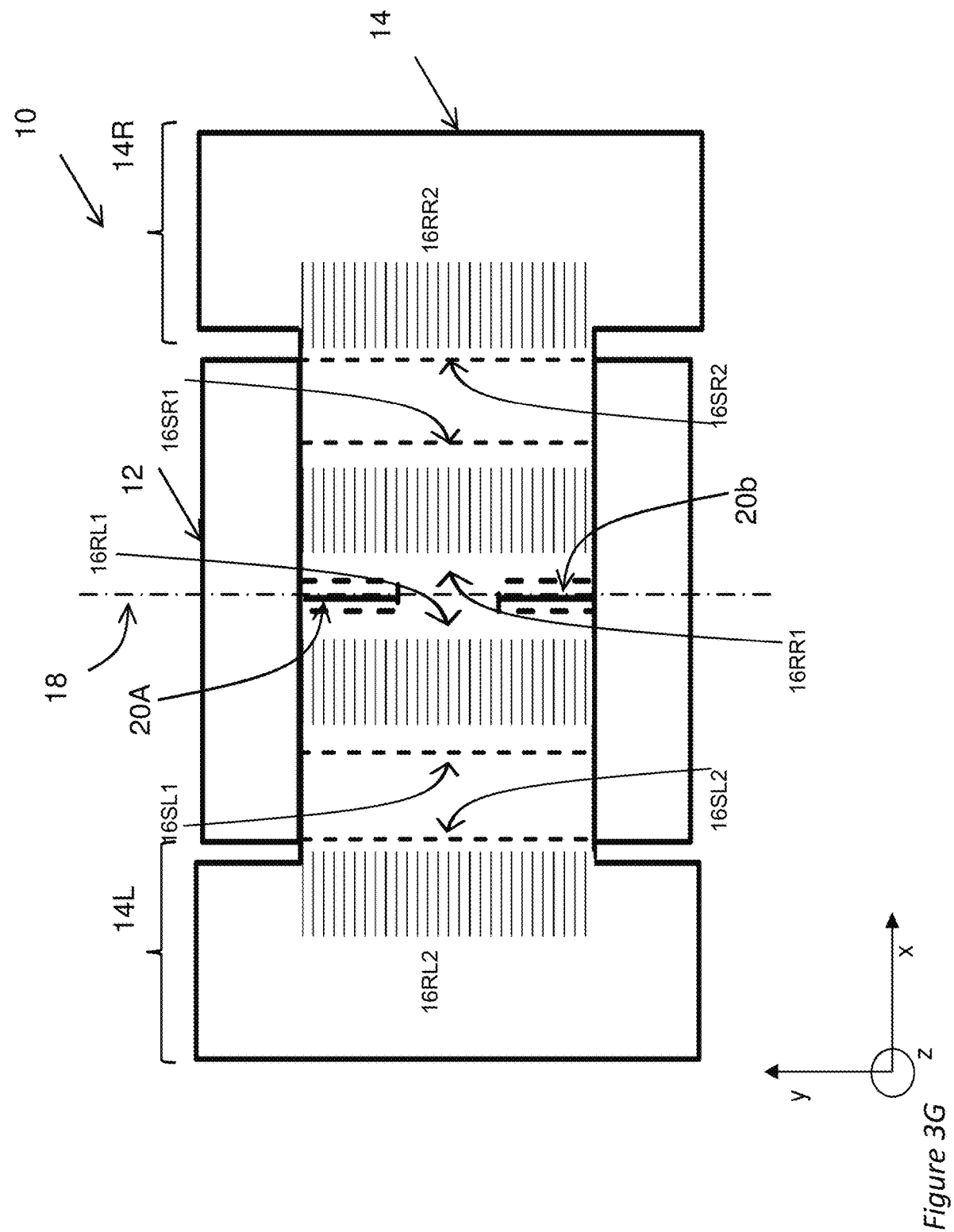
FIG. 3G is a top view along the z-axis of the embodiment of FIG. 3A, showing additional hidden features.

As can best be seen in FIG. 3F, the MEMS mirror 10, as shown in FIG. 3, comprises a first substrate layer HL1, a second substrate layer HL2, and an actuator layer AL that is sandwiched between the first and second substrate layer. The first substrate layer, the second substrate layer, and the actuator layer together form a stator 12, a rotor 14, and an actuator 16 to enable the rotor to rotate relative to the stator along the rotation axis 18, for example within a rotation range of maximum +/−10 degrees, as can best be seen in FIG. 3E. The rotation axis lies in a reference plane RP, being defined by the actuator layer in the neutral state of the rotor.

As shown in FIG. 3F, the actuator layer may comprise a first and a second mutually insulated device layers DL1 and DL2 respectively of an electrically conducting material. DL1 is arranged at a side of the reference plane facing the mirror surface 14MS, while DL2 is arranged at a side of the reference plane facing the stator. DL1 and DL2 respectively form a first and second electric figpole in each of the comb elements. In the embodiment shown, the first electric poles of each of the comb elements of the rotor are electrically interconnected via an eutectic bond with the first substrate layer HL1, and are electrically connected to an output of a driver, via bond pads 22 on the mirror (FIG. 3C). In an application, such as the probe 50, the at least one of a first and a second electric pole of each of left and right comb elements of the stator may be coupled to a respective feedback input of a driver, wherein the left and right comb elements of the stator are arranged at mutually opposite sides of the rotation axis, such that the MEMS mirror is rotation symmetric. The bipolar construction of the comb elements enables an accurate measurement of the amplitude and the moment of zero-crossing of the rotor.

As illustrated in FIG. 3F, the rotor comprises a rotor body 14RB and a rotor support 14RS. The rotor support, fixed at a first face of the rotor body, keeps the rotor body at a distance from the stator sufficient to enable the rotor to operate within its specified rotation range, for example the exemplary range from −10° to +10°, as is depicted in FIG. 3E. The rotor body 14RB has a mirror surface 14MS at a second face, opposite to its first face. The mirror comprises the stator 12 and the rotor support 14RS at mutually opposite sides of the reference plane RP. In the embodiment shown in FIG. 3F, the respective comb-elements of the actuator are electrically connected to respective bond pads forming electric contacts. The electric contacts denoted as 1: MIR_C, DL1 and 5: MIR_C, DL1 are connected to the device layer DL1 of the rotor comb elements 16RL1 and 16RR1 and further electrically connected via the handle layer HL1 to the rotor comb elements 16RL2 and 16RR2. The electric contacts 2: MIR_L_HND, DL1 and 6: MIR_R_HND, DL1 are connected to the device layer DL1 of the pair of stator comb elements 16SL1, 16SL2 and to the device layer DL1 of the pair of stator comb elements 16SR1, 16SR2 respectively. Furthermore, 3: MIR_L_DEV, DL2 and 7: MIR_R_DEV, DL2 are connected to the device layer DL2 of the pair of stator comb elements 16SL1, 16SL2 and to the device layer DL2 of the pair of stator comb elements 16SR1, 16SR2 respectively. In the embodiment shown, two further contacts 4: NC and 8: NC are shown to the second handle layer HL2. In practice not all electrical contacts 1-8, e.g. the electric contacts 4: NC and 8: NC in this example, need to be connected to an external conductor.

In an alternative embodiment, the stator 12 may further comprise through silicon vias that electrically connect respective comb-elements of the actuator 16 to respective electric contacts at a surface 14S″ of the stator facing away from the mirror surface. Furthermore the torsion beams may serve as an electrical connection to electrically connect comb elements of the rotor via a through silicon via to an electric contact. Therewith the mirror 10 can for example be electrically connected to conductors in a circuit board carrying the mirror. In this way, using through silicon via technology, the bondpads 1: MIR_C, DL1 etc. as shown in FIG. 3F are obviated, which enables an increase of size of the mirror surface 14MS in a direction of the rotation axis 18 to at least 90%, e.g. 100% or even larger of the size of the stator in said direction.

In the embodiment shown, the rotor body 14RB has peripheral portions 14L, 14R that extend beyond the stator 12 in transverse direction x, −x. These peripheral portions are transverse to the rotation axis 18 and are aligned with the reference plane. These peripheral portions 14L and 14R can have a respective extension portion 14L1 and 14R1 respectively at a distance along a respective side face of the stator, as is depictured in FIG. 3B. 14L1 and 14R1 decrease the resonance frequency of the MEMS mirror. A relative low resonance frequency, for example in the range of 200-4.000 Hz, contributes to obtain high quality OCT images. At relatively high resonance frequencies, the lateral resolution will be lower which complicates distinguishing small structures in the image.

The actuator 16 comprises at least a first comb pair 16SL1 fixed to the stator, and 16RL1 fixed to the rotor support 14RS, and a second comb pair 16SR1 fixed to the stator and 16RR1 fixed to the rotor support 14RS, as is depictured in FIG. 3D. Optionally, the actuator can comprise at least one further pair of mutually interdigitated comb elements, including at least a third comb pair 16SL2 fixed to the stator and 16RL2 fixed to a peripheral portion of the rotor body, and a fourth comb pair 16SR2 fixed to the stator and 16RR2 fixed to the peripheral portion of the rotor body.

Figure 3H:
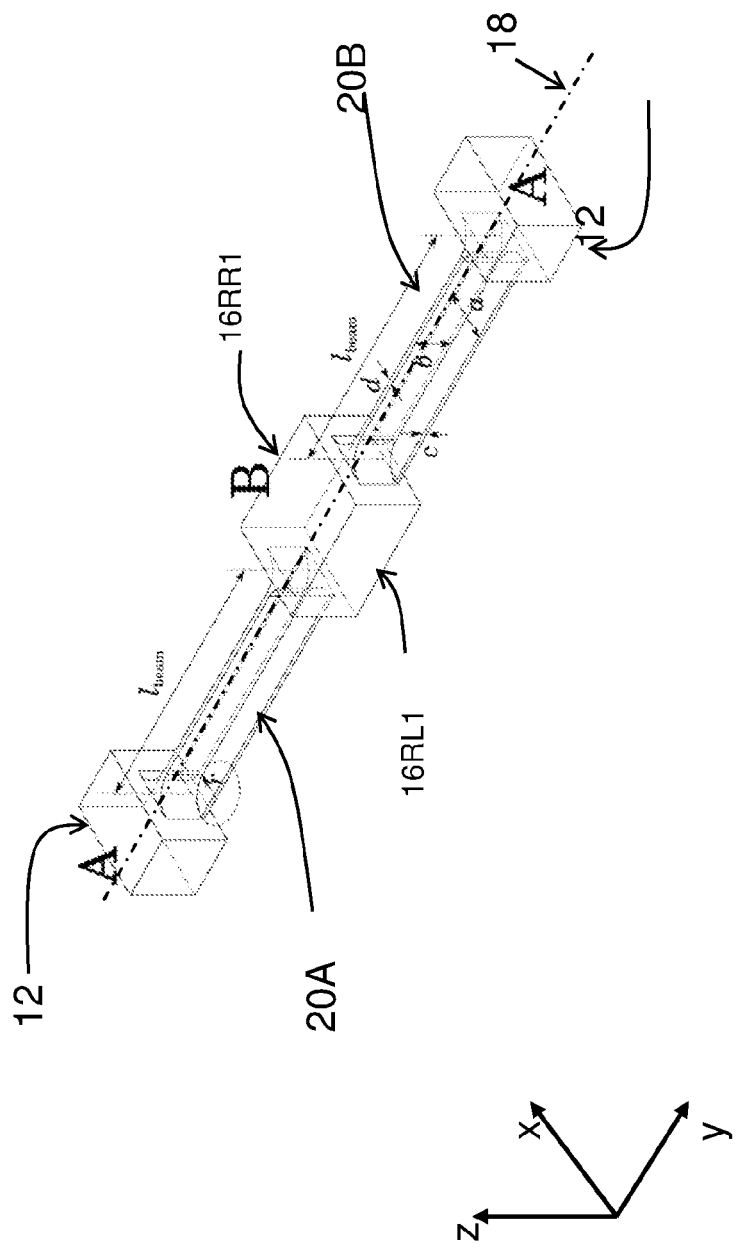
FIG. 3H is a perspective view of a part of the embodiment of the MEMS-mirror of FIG. 3A.
Figure 3I:
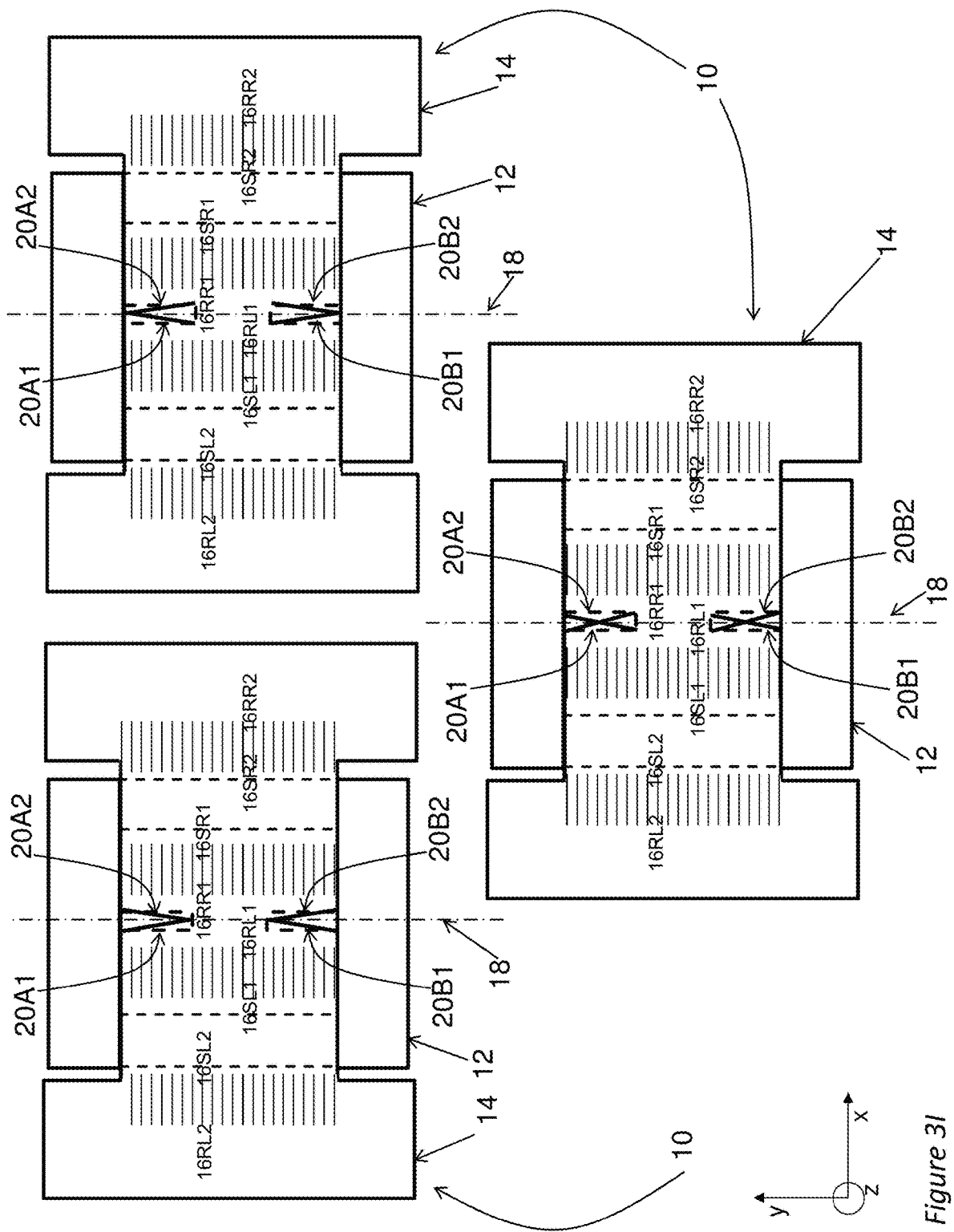
FIG. 3I shows 3 versions of the same top view along the z-axis as is represented in FIG. 3H, with 3 different options for possible torsion beam configurations.

At mutually opposite sides the actuator (at the rotation support RS) is coupled with the stator via a torsion beam 20A, 20B, of which an embodiment is represented in FIG. 3H. The torsion beams extend along the rotation axis 18 to the stator. The torsion beams may have a T-shaped cross-section in a plane perpendicular to the rotation axis, i.e. an elongate structure having a first and a second blade like portion both extending in the longitudinal direction of the torsion bar and in cross-section being arranged orthogonal with respect to each other such that a lateral side of the second blade is joined to a centre of a main side of the first blade. In an embodiment thereof the first blade is arranged in a plane parallel to the reference plane defined above and its main side faces the rotor body. The first blade can be in DL2, while the second blade can be in DL1. Other shapes of the torsion beams are also possible, where the key requirement is that the torsion beams should allow a rotation of the rotor body with low stiffness, to allow a low resonance frequency, and have low stress at large tilt angles. It should be stiff in other directions and rotations, to resist other movements. Therefore, the ratio between the height and the thickness of the rotation beams is important. The beams can either be high and thin or broad and low. As a further alternative, the mirror may be suspended at each side to a pair of torsion beams (20A1, 20A2, 20B1, 20B2) that are connected at one end under a slight angle, max. 20 degrees, as shown in FIG. 3I. The triangle shape resists rotations in the horizontal plane, while the beams itself resist movement in the vertical plane.

Figure 7:
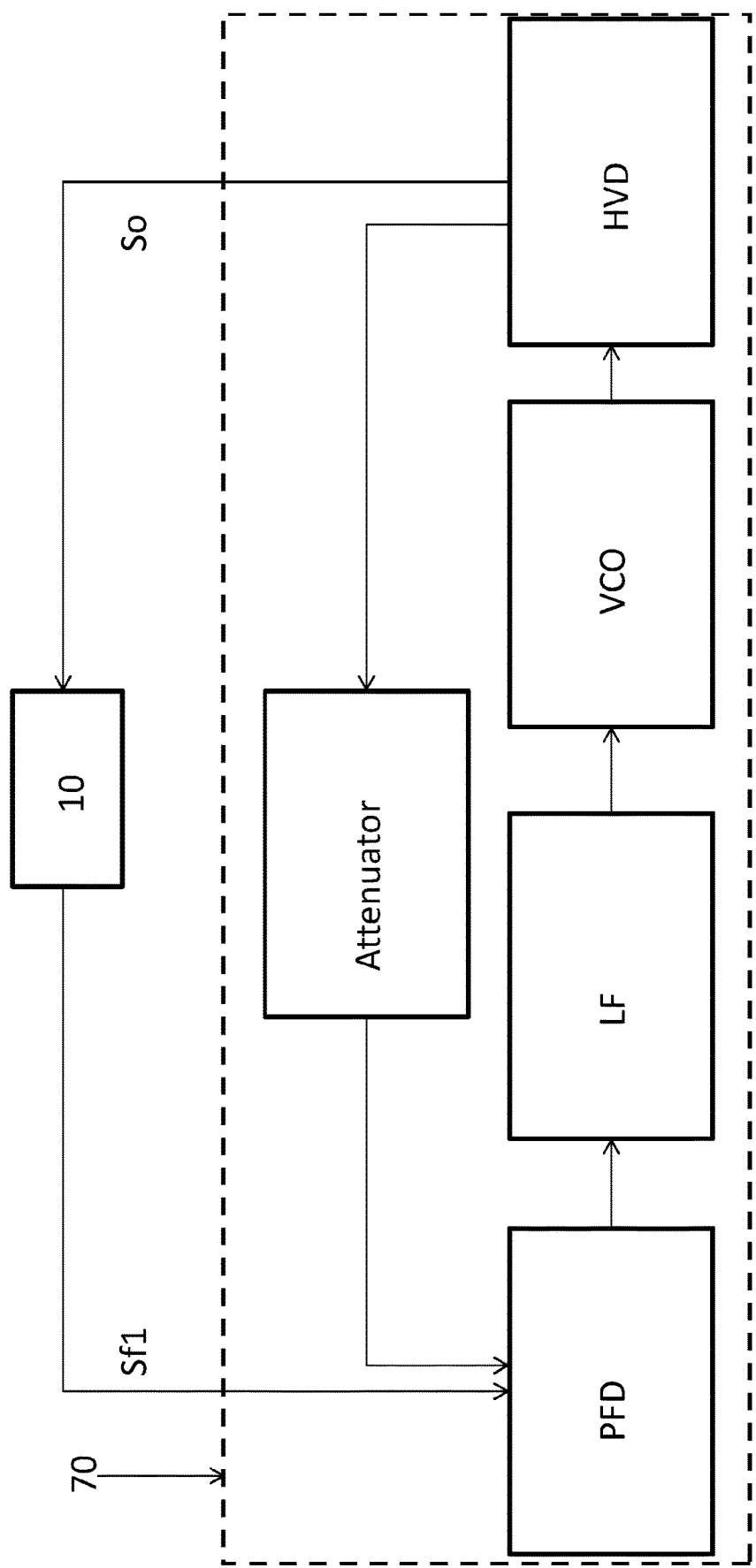
FIG. 7 is a block schematic drawing of an embodiment of a driver for the MEMS mirror.

In an embodiment a driver 70 is accommodated inside the housing 51 of the probe. The accommodation of the driver close to the MEMS-mirror further improves an accuracy of actuation and control thereof. The driver in FIG. 7 is at least provided with a feedback input to receive a feedback signal Sf1, and an output to provide a drive signal So to the actuator 16 of the MEMS mirror. The feedback signal Sf1 is indicative for a rotational state of the rotor, and relates to the amplitude, frequency or position of the mirror rotation. Information about the mirror rotation can be a zero-crossing signal.

The driver, which may be implemented in an application specific IC (ASIC) may function as a phase-locked loop PLL. This phase-locked loop may comprise a phase frequency detector PFD, a voltage controlled oscillator VCO, a loop filter LF, a high voltage output driver HVD, and a feedback attenuator as schematically shown in FIG. 7.

The driver may be operable in a sweeping mode, which is the start-up mode, and a normal operating mode succeeding the start-up mode. In the sweeping mode, starting from a standstill of the rotor body a high voltage square wave is applied to the actuator, to start a sweeping state. During this state the VCO frequency is slowly decreased, until the MEMS mirror starts to resonate. Once the amplitude of the mirror is above a certain threshold that indicates that reliable phase detection is possible, the ASIC switches from sweeping mode to the normal operating mode controlled by the PLL, to lock the MEMS mirror at its resonance frequency. The PFD detects the phase difference between the zero-angle crossing of the MEMS mirror, and the falling edge of the actuation signal, which is necessary to be able to operate the mirror in resonant mode.

At resonance frequency the MEMS mirror rotates stably, with the predefined maximum amplitude. Another benefit of operation at the resonance frequency is that a low voltage is sufficient to sustain the operation.

Figure 1:
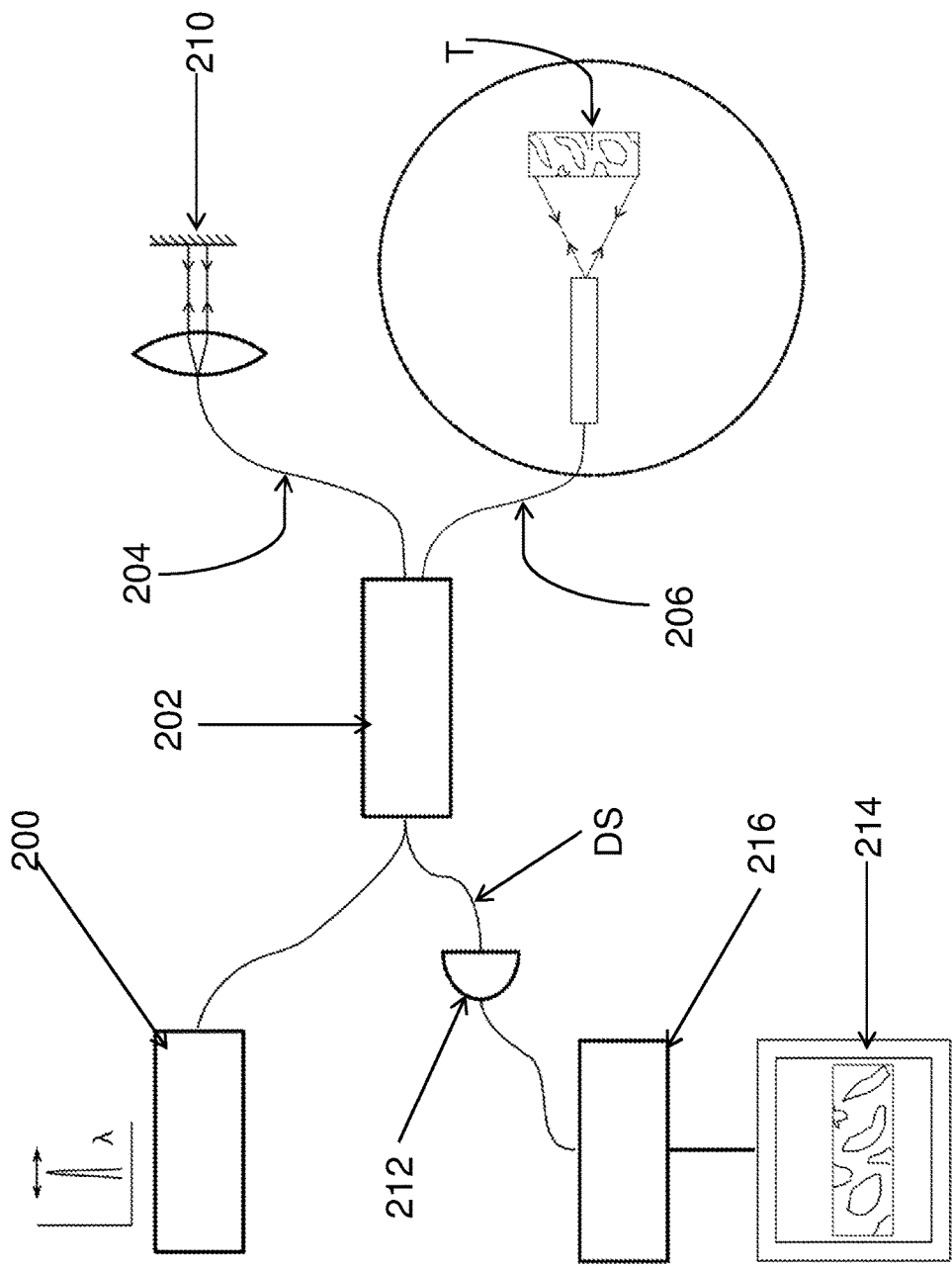
FIG. 1 schematically shows a swept source OCT system.
Figure 4:
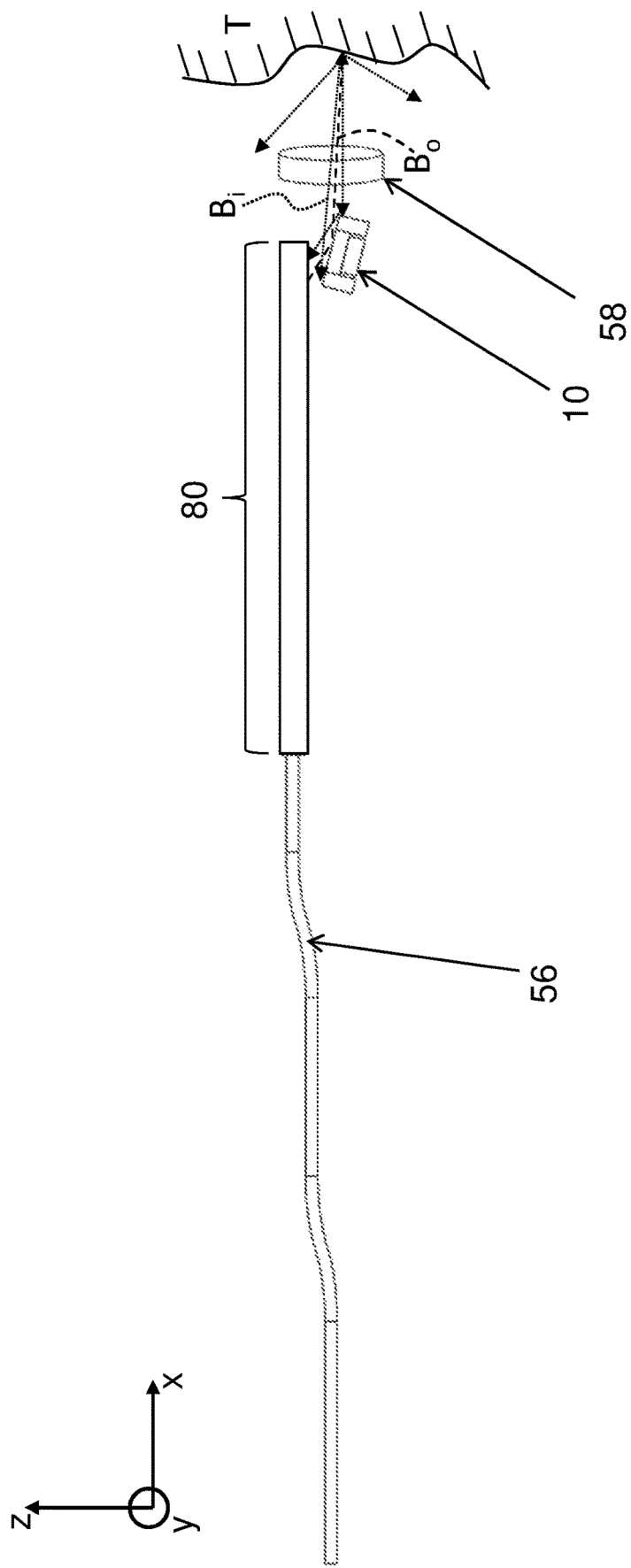
FIG. 4 schematically shows an embodiment of the optical assembly, to transport the light from the swept source system to the tissue and back to the system.

FIG. 4 schematically shows an optical assembly 80 for guiding a light beam Bo, received via beam guide, such as a single mode fibre 56 from a light source, such as a tuneable laser source 200 of FIG. 1 via the MEMS mirror 10, towards a tissue T to be examined and to guide light beams Bi, subsequently reflected by the tissue T and by the mirror 10 back via the beam guide 56 for processing and analysis. The optical assembly is part of an optical path that further comprises the MEMS mirror 10 and the viewing window 58. A prism directs the light beam in such a way on the MEMS mirror that the light beam exits the probe via the viewing window in the longitudinal direction of the probe. The emanating light beam can be under a very slight angle of e.g. 10 degrees with the longitudinal axis of the probe.

The housing 51 of the probe may comprise a top part 53, (see FIG. 6) and a carrier part 52, see FIG. 5A, 5B, 5C, which protect the optical and electrical components and keep them aligned. The carrier part 52 of the housing 51 (FIG. 5A-C), has a main portion 32 extending in a direction substantially coinciding with a longitudinal direction x of the housing, and an end portion 34 facing the viewing window. The main portion carries the driver, while the end portion carries the MEMS mirror. The carrier part at a side carrying the MEMS mirror is tilted with respect to said longitudinal direction. The end portion of the carrier may be provided with recesses 36, see FIG. 5C facing the peripheral portions 14L1, 14R1 of the rotor body 14RB, to enable rotation through the full rotation range. Alternatively, the stator 12 of the MEMS mirror can be placed on an elevated part on the end portion of the carrier, e.g. a pedestal, to enable rotation through the full rotation range.

Figure 6:
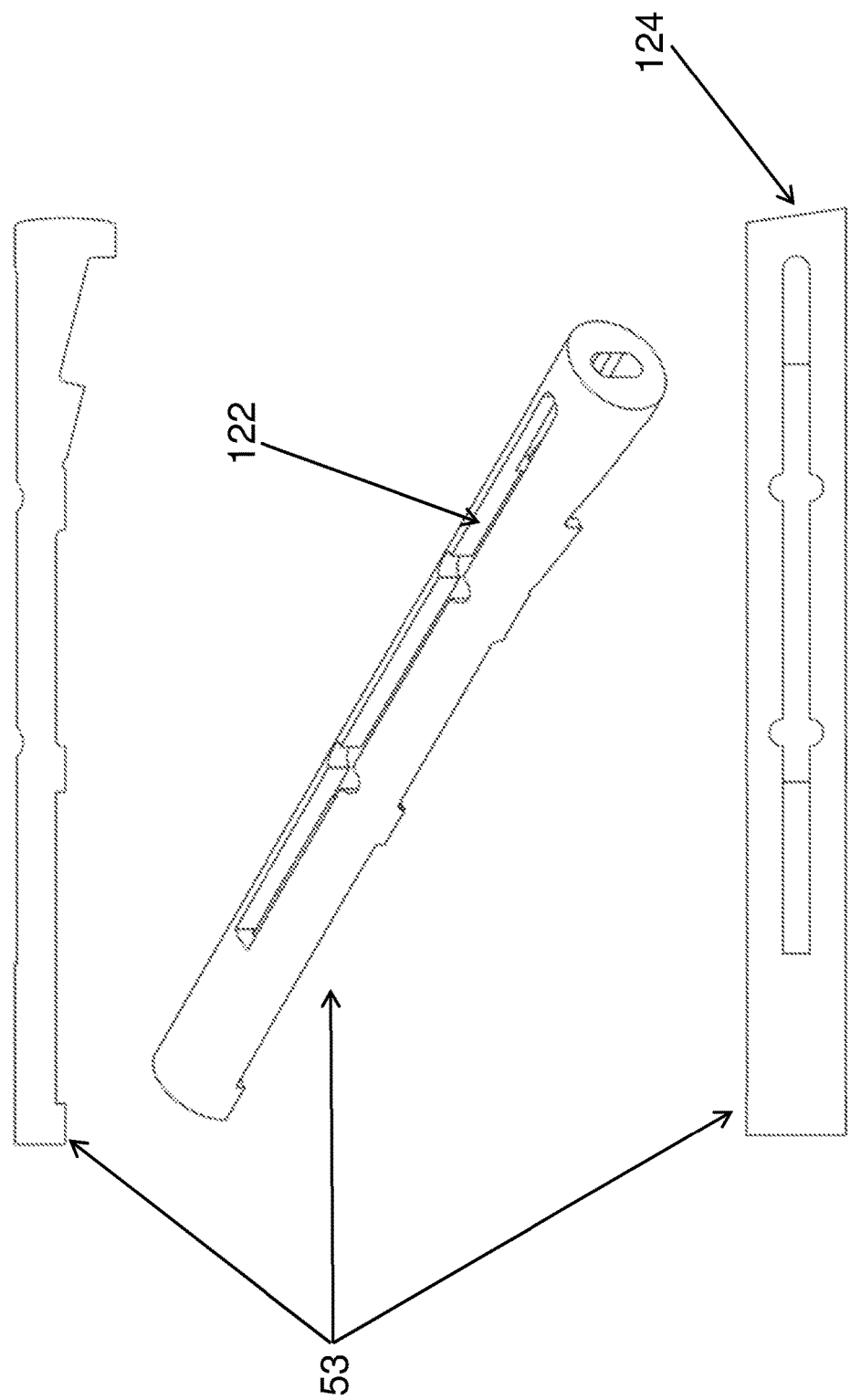
FIG. 6 schematically shows an embodiment of the top part of the housing of the probe.

The top part 53, as shown in FIG. 6 may protect the electrical components and align the optical assembly, for which it is provided with a slit 122. The top part may allow for positioning of the viewing window 58 under an angle of e.g. 8 degrees 124 to avoid static back reflection.

The probe is made for use with a swept source OCT system, which may include a tuneable laser as light source. In an embodiment, the tuneable laser has a power of 10-50 mW, a centre frequency of 1060 nm, a bandwidth of around 100 nm, and a spectral sweep rate of at least 100 kHz.

Figure 8A:
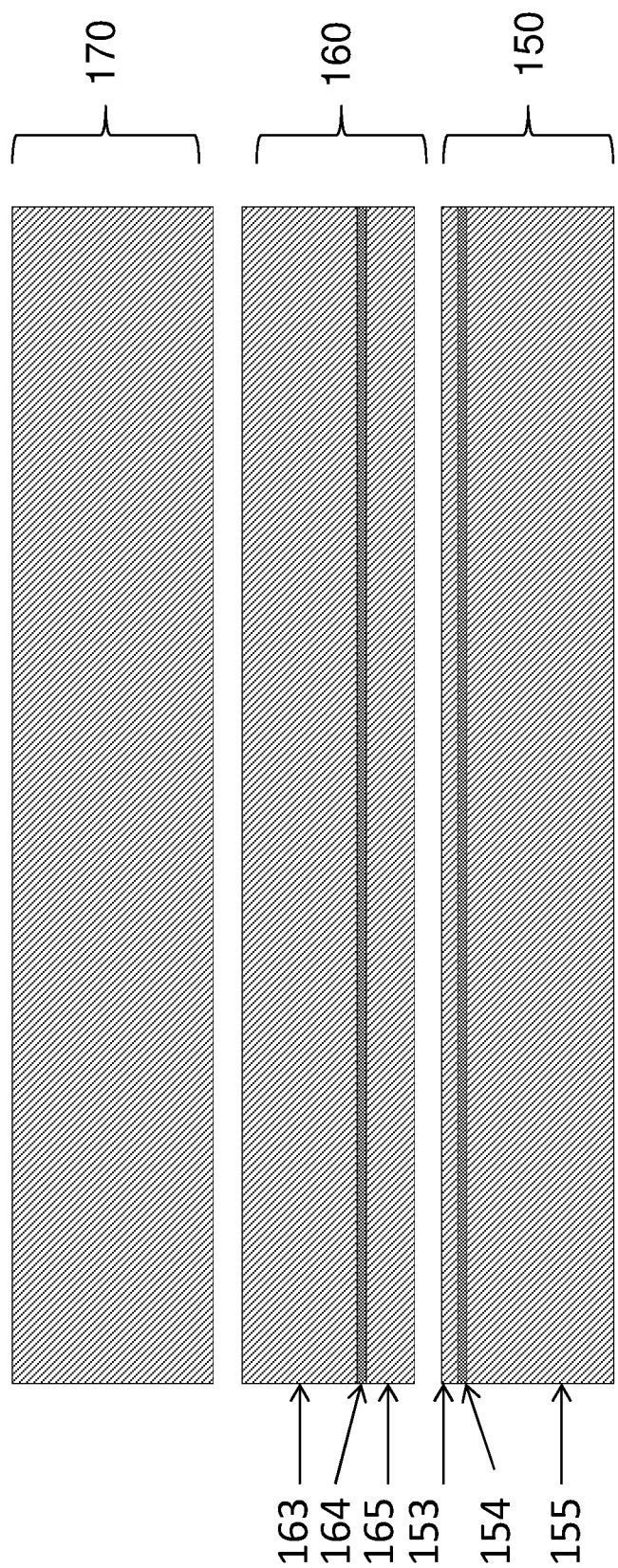
FIG. 8A-8U schematically shows subsequent steps of a possible manufacturing method for the described MEMS mirror.
Figures 8B, 8C:
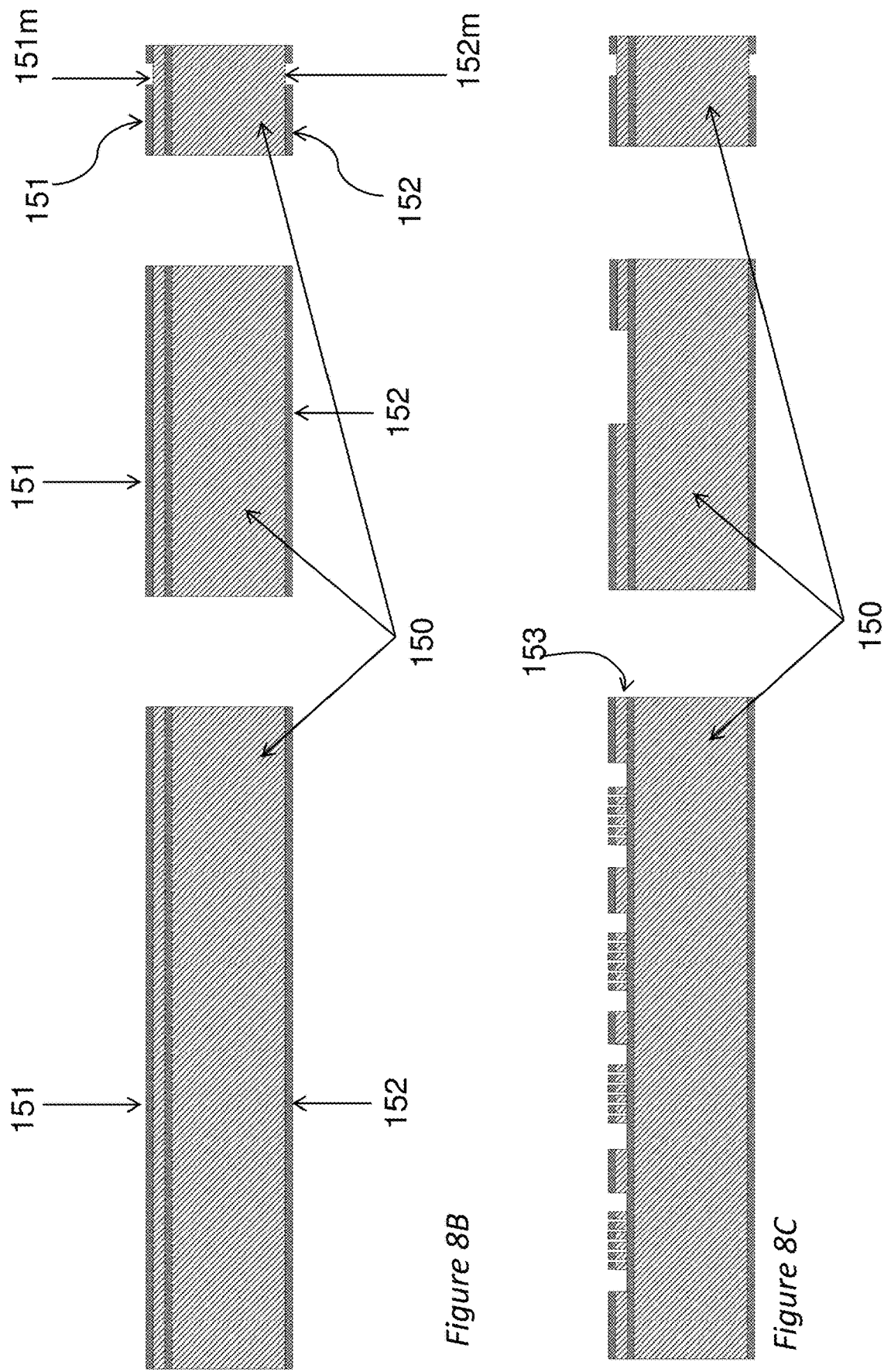
Figures 8D, 8E:
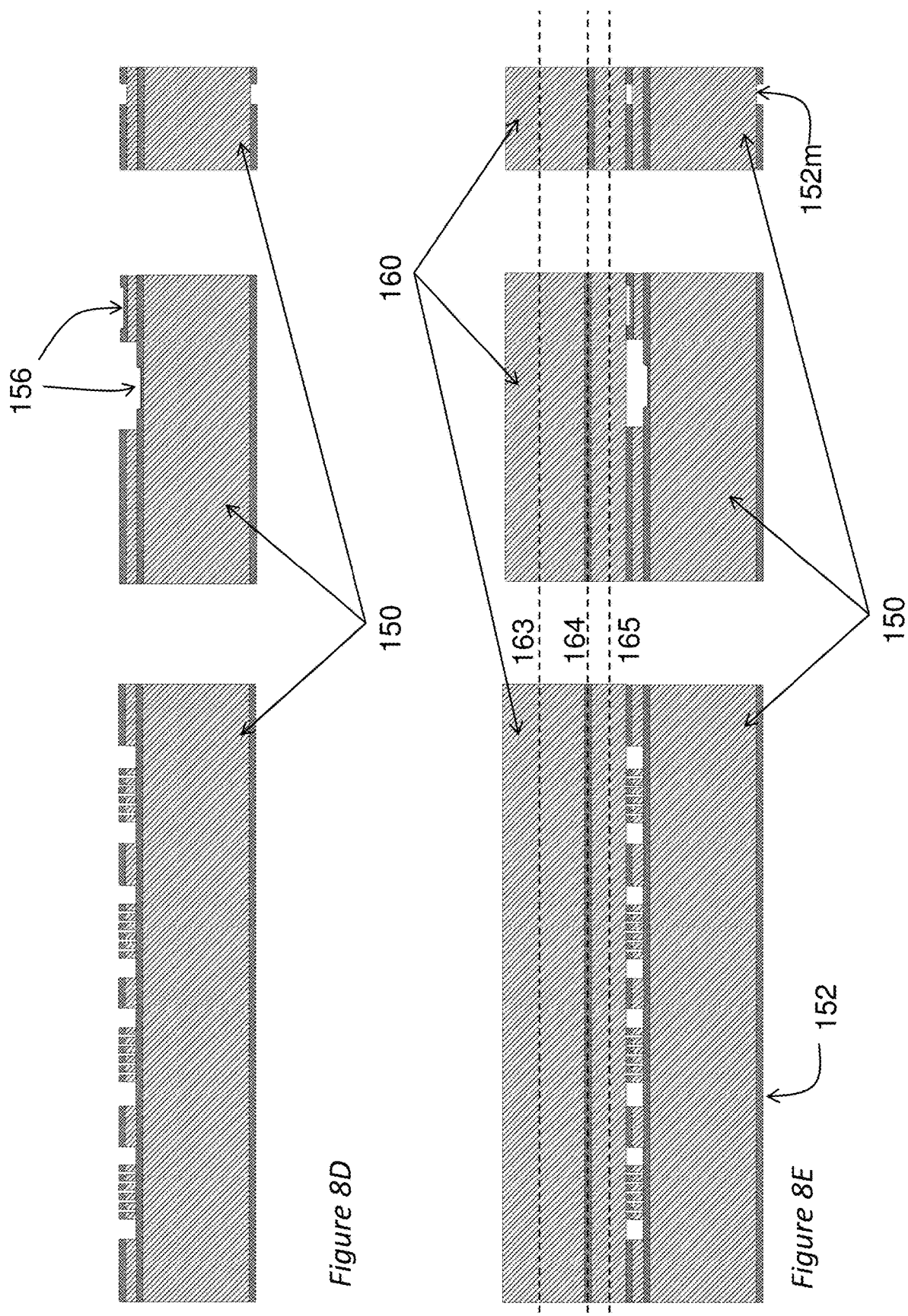
Figures 8F, 8G:
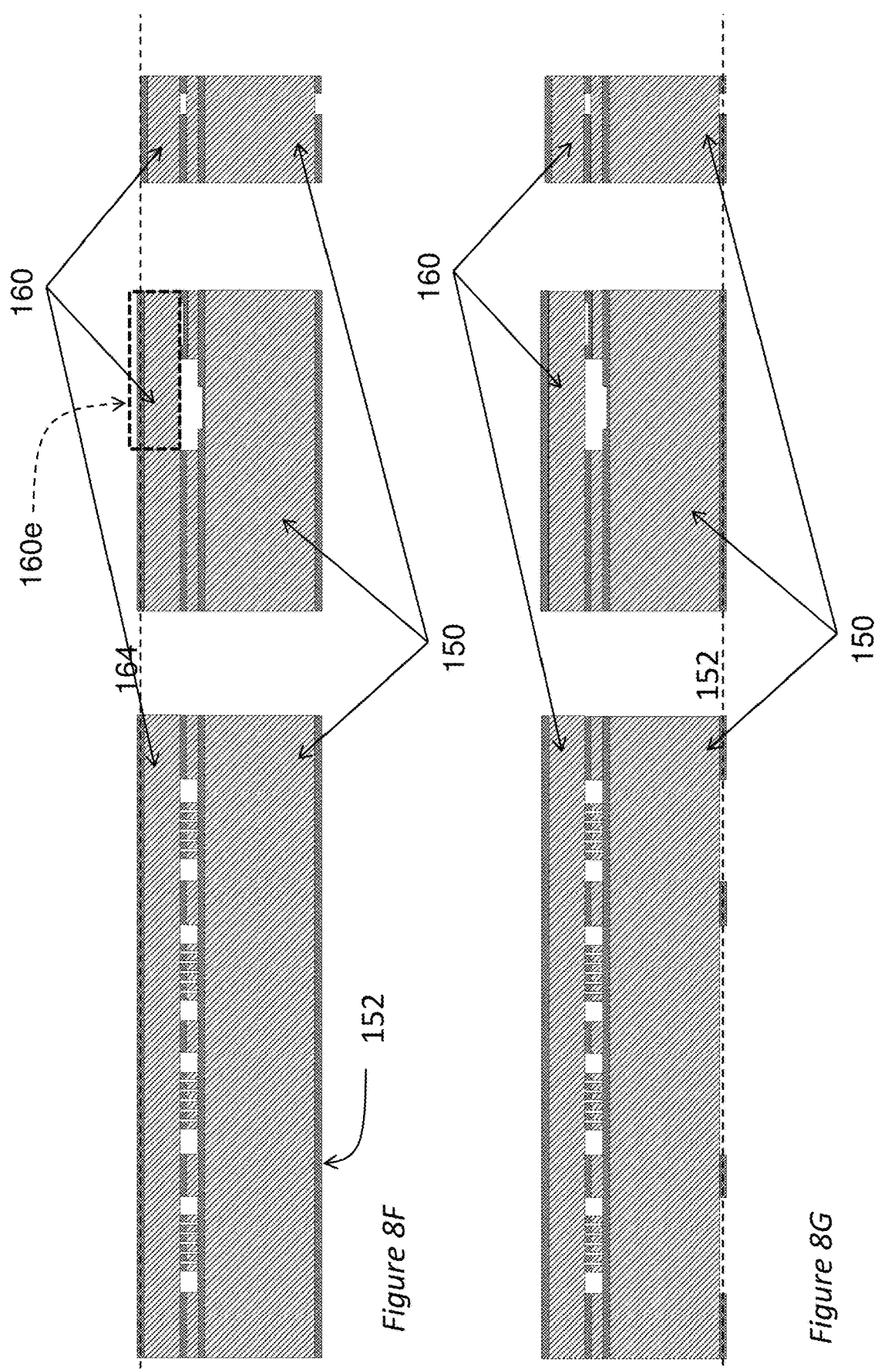
Figures 8H, 8I:
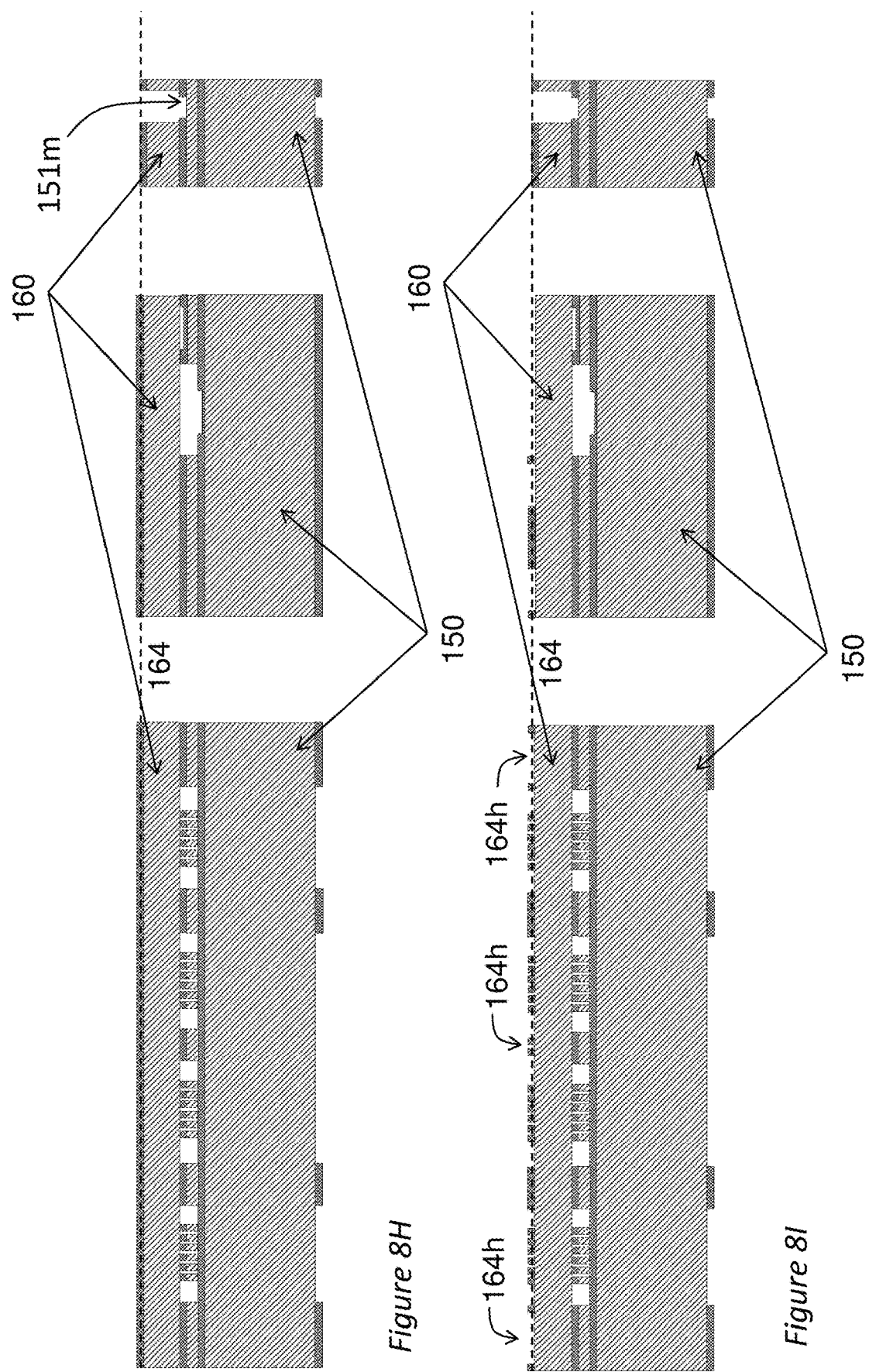
Figures 8L, 8M:
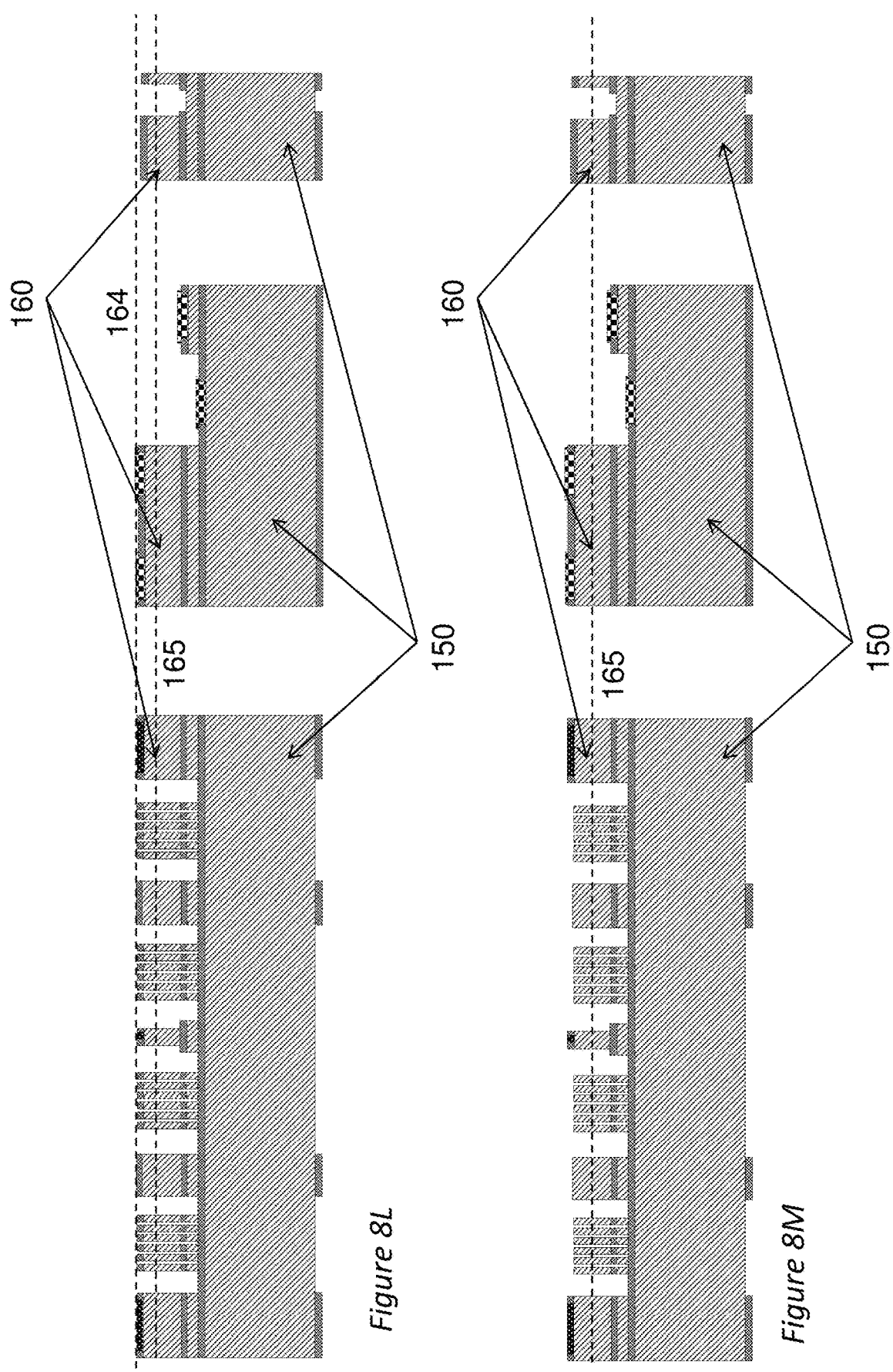
Figure 8N:
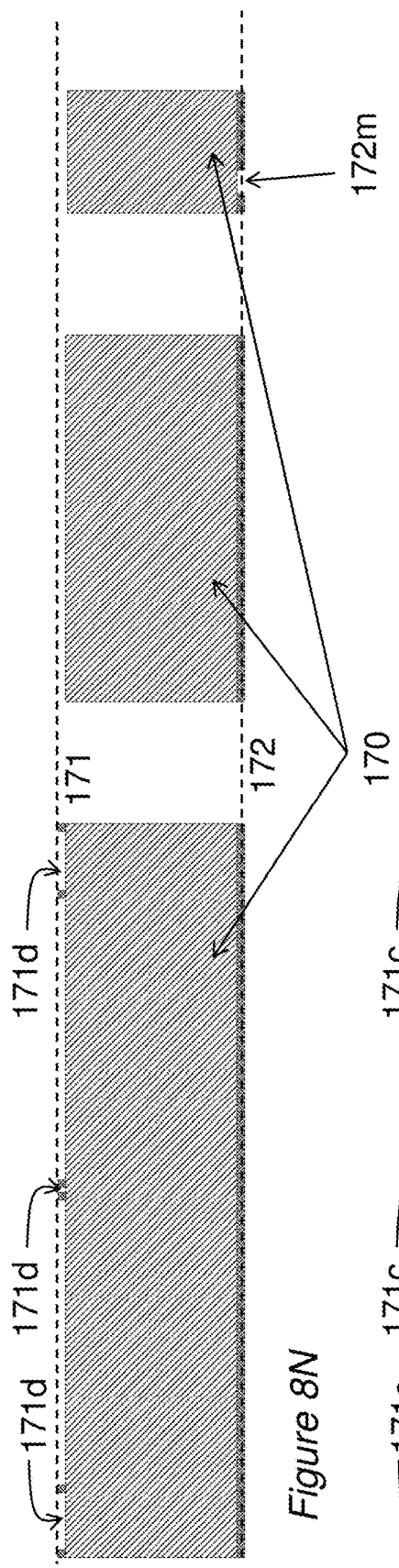
Figure 8O:
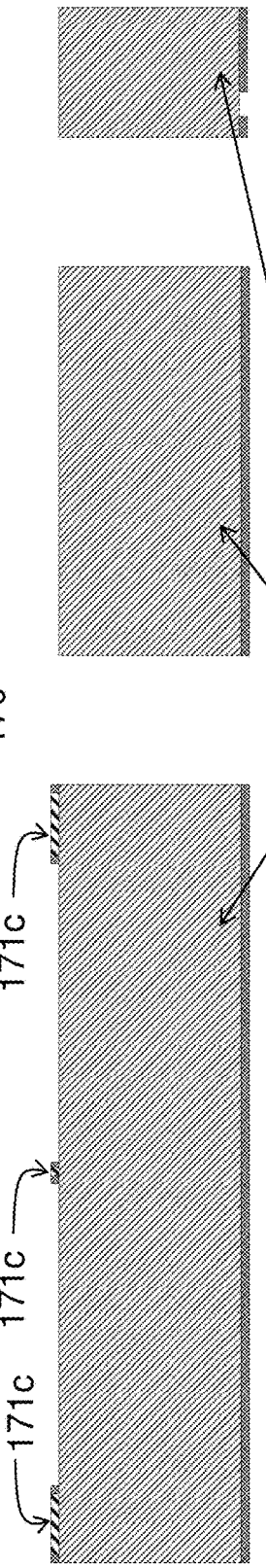
Figure 8P:
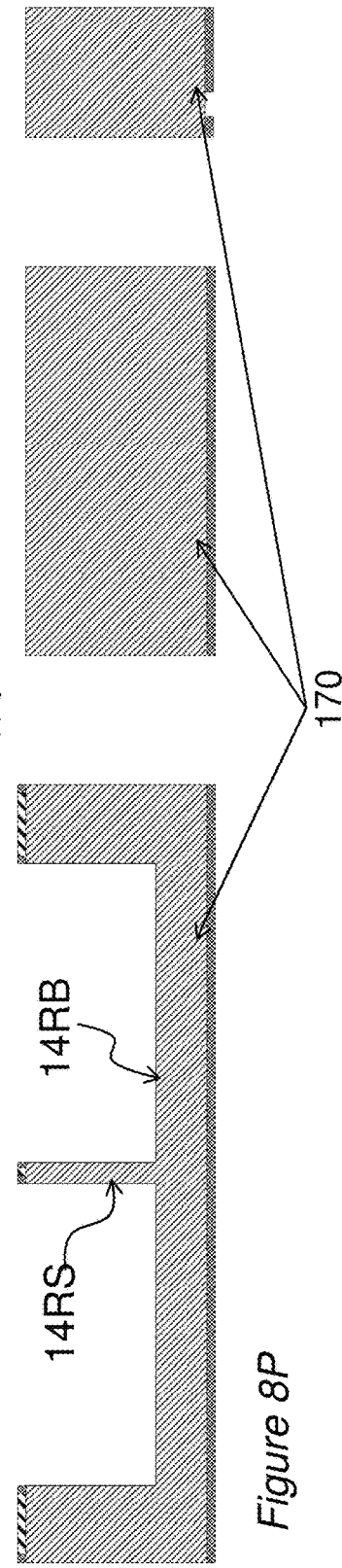
Figure 8Q:
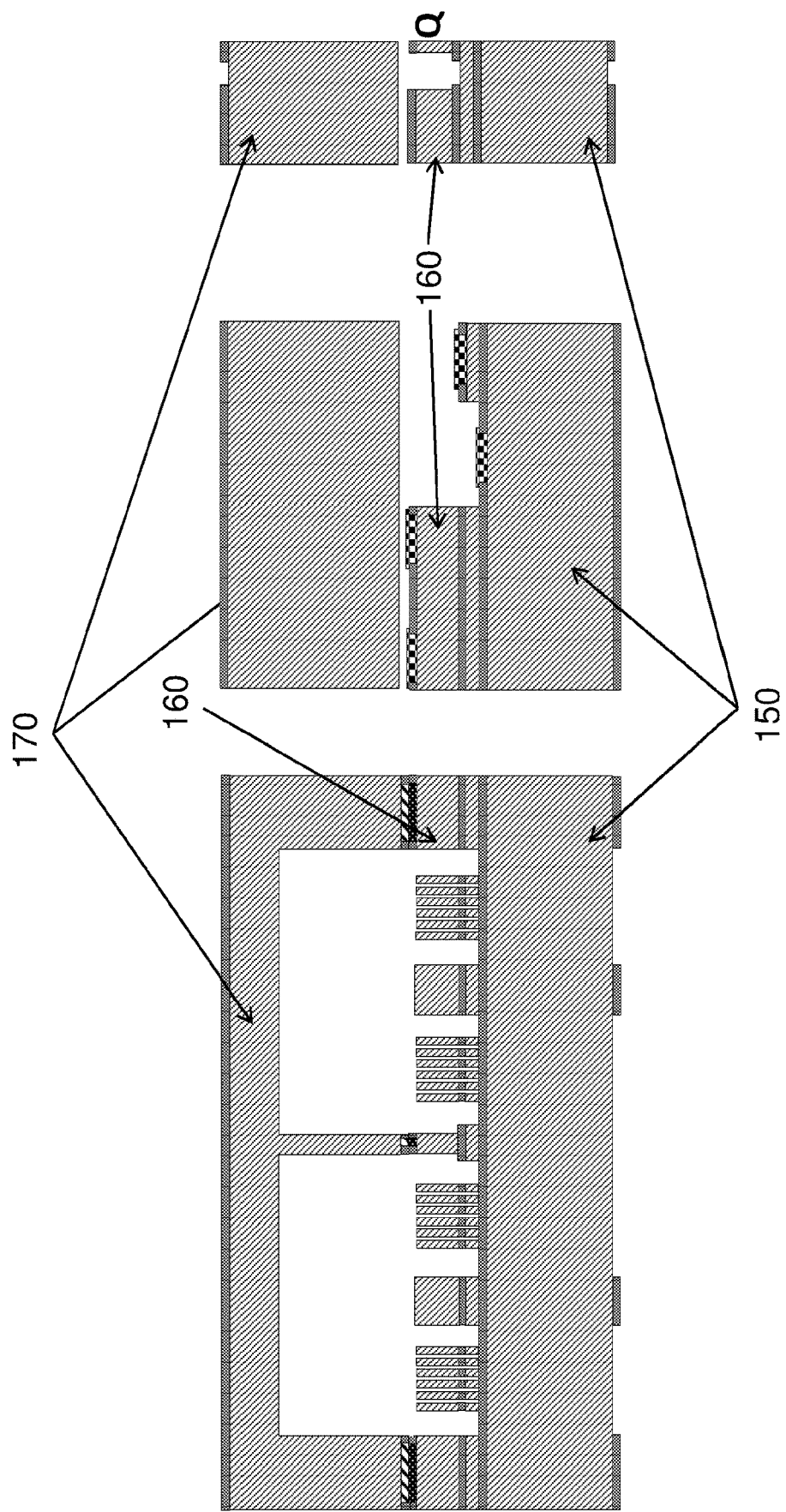
Figure 8R:
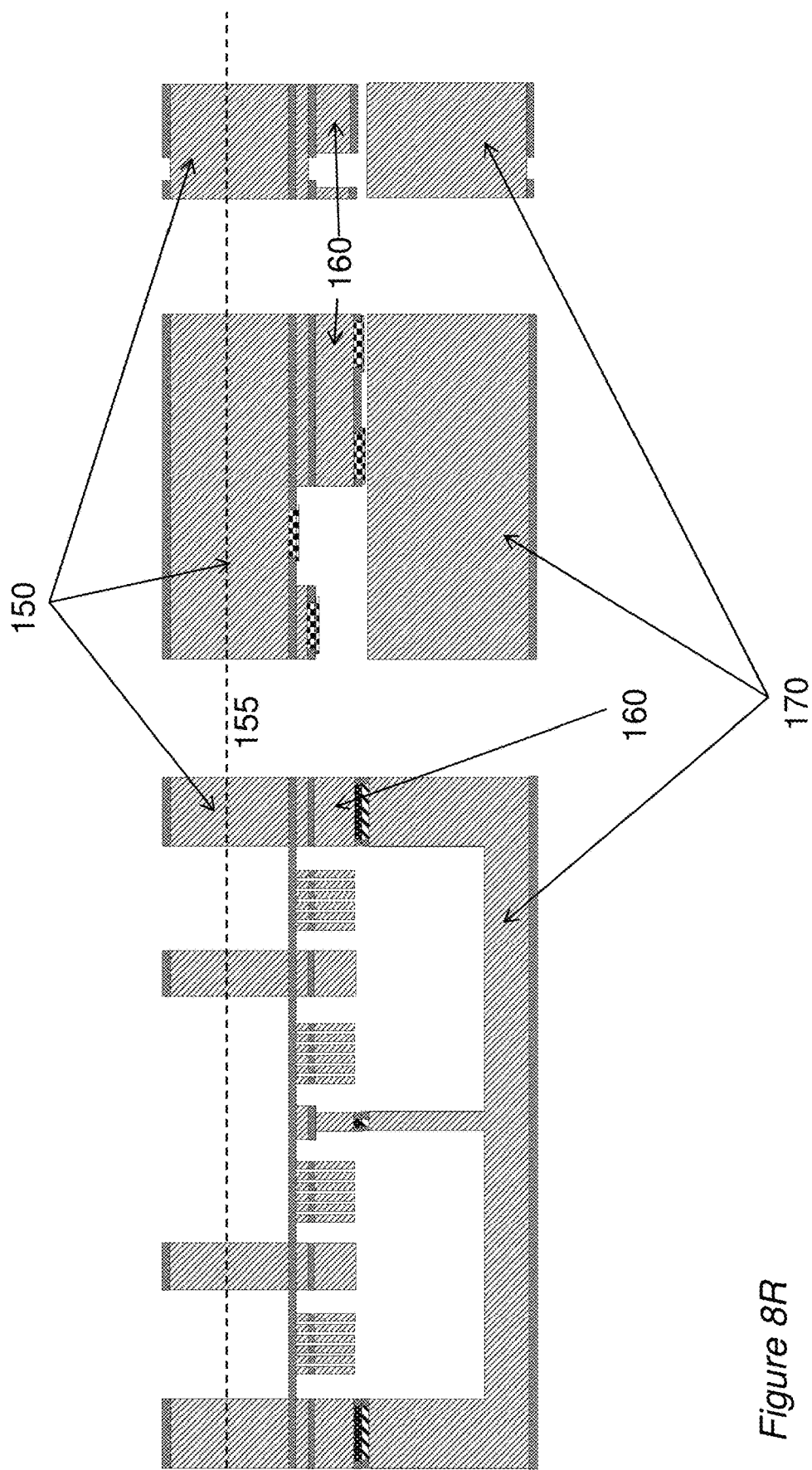
Figure 8S:
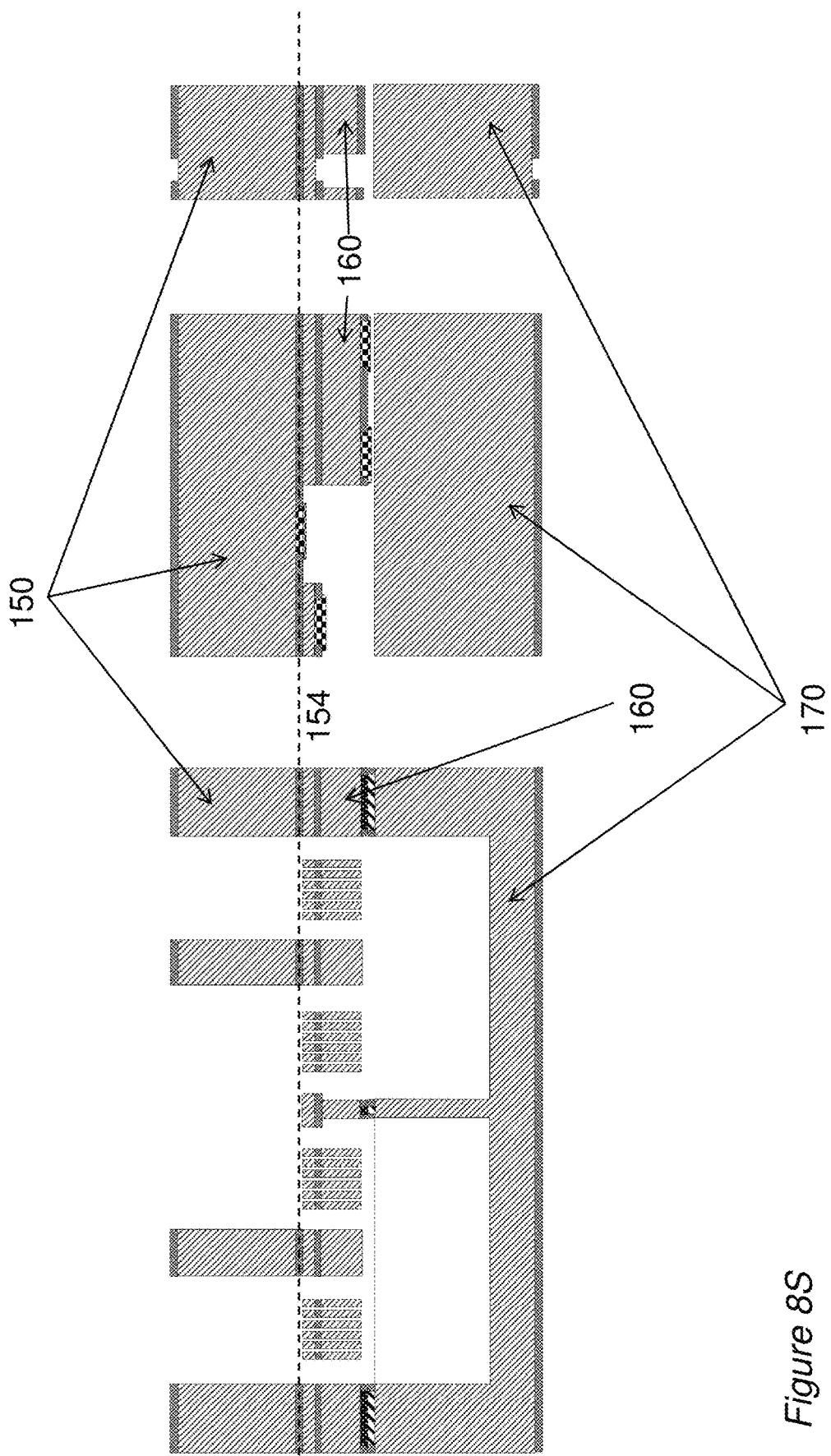
Figure 8T:
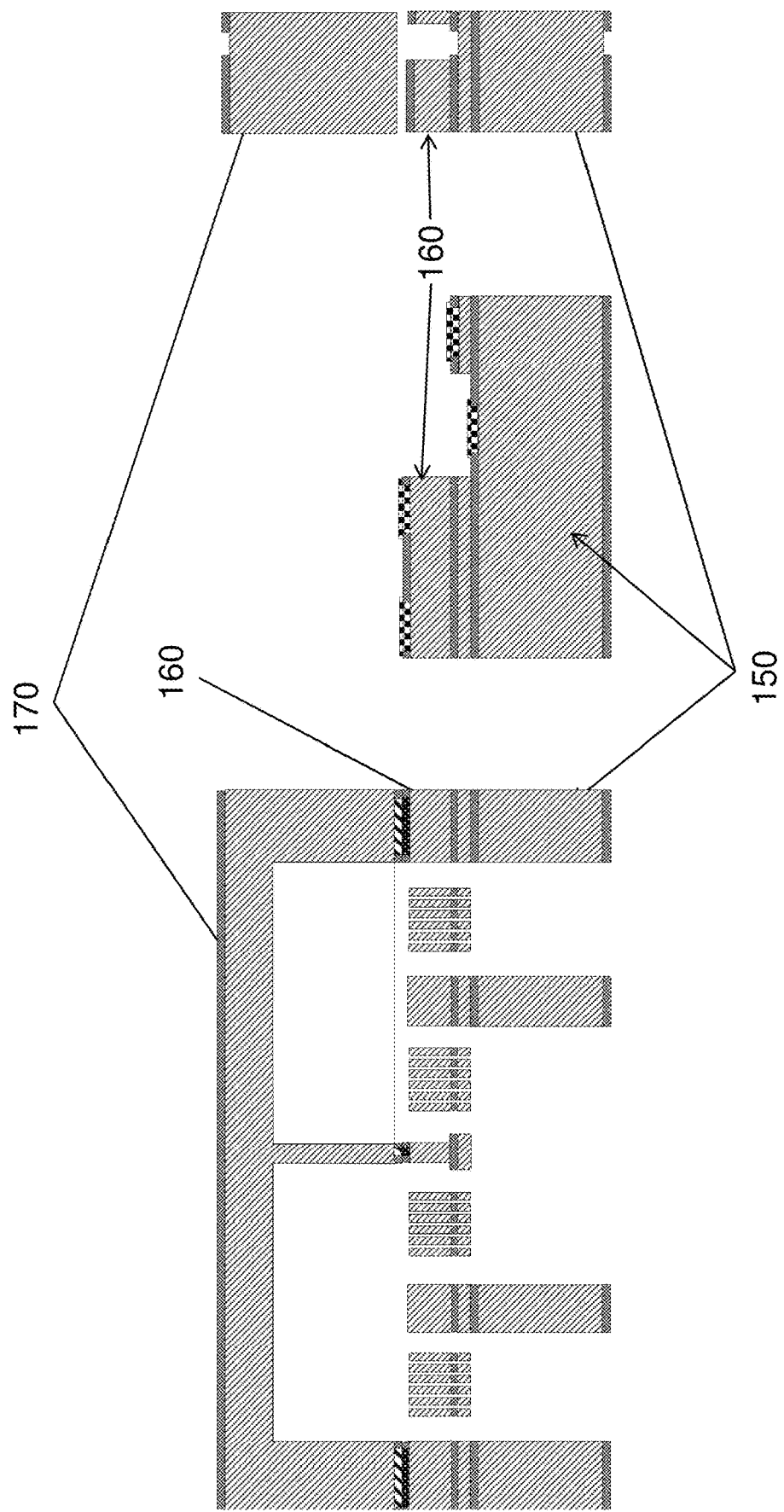
Figure 8U:
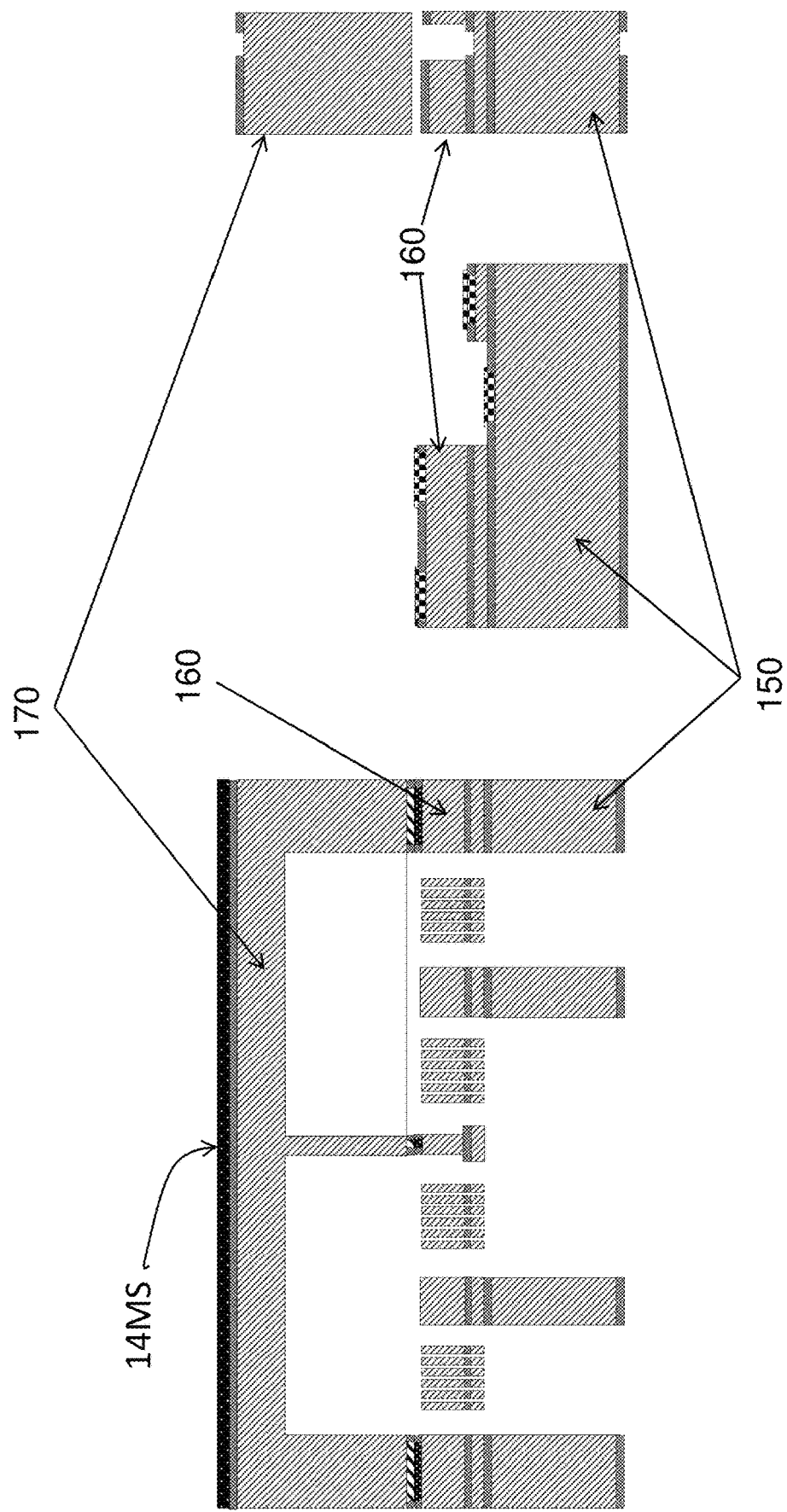

An exemplary method of manufacturing the MEMS may proceed as illustrated in FIGS. 8A to 8U. In each of FIGS. 8B through 8U three cross-sections are shown from left to right. These are respectively taken according to I-I, II-II in FIG. 3C, and the cross-section on the most right shows the process steps on the alignment marker of the wafer.

In the exemplary method a MEMS mirror is manufactured from a first wafer 150, a second wafer 160 and a third wafer 170 as shown in FIG. 8A. Therein the first wafer 150 is used to form a base layer and a first comb layer (DL2), the second wafer 160 is used to form a second comb layer (DL1). The third wafer 170 is used to form the rotor body and rotor support layer. The wafers 150, 160, 170, e.g. silicon-on-insulator (SOI) wafers, may have a thickness, but not necessarily mutually the same thickness, in the order of a hundred micrometers to a few hundreds of micrometer. In the embodiment shown the wafers each have a thickness of 300 μm. The first and the second wafer 150, 160 are SOI. The first wafer 150 comprises a first and a second silicon layer 153, 155 insulated by an insulator layer 154. The second wafer 160 comprises a first and a second silicon layer 163, 165 insulated by an insulator layer 164. Alternatively, the first SOI wafer 150 and second SOI wafer 160 can be replaced with one DSOI wafer, which comprises 3 insulator layers and 4 silicon layers.

The insulator layers 154, 164, for example siliconoxide layers, may for example have a thickness of a few hundred nm to a few micrometer, for example a thickness of 1 μm. The exposed surface 151, 152 of the first wafer 150 may be protected with thermal oxidation, after which front—and/or backside alignment markers 151*m*, 152*m* can be etched (FIG. 8B). After that, the pattern of the comb drives and the torsion beams to be formed can be translated to the wafer via a mask lithography step, and this pattern can be etched in the first silicon layer 153 via DRIE etching (FIG. 8C). After this, via a partial-oxygen-etch holes 156 for the future bond pad locations can be opened (FIG. 8D).

In a next step the second wafer 160, that is to form the second comb layer may be bond to the first wafer 150 via fusion bonding (FIG. 8E). The second wafer 160 can then be ground back to the siliconoxide layer 164 of 0.2 μm (FIG. 8F). Next, the assembly of the first and the second wafer can be turned around and the backside 152 can be etched (FIG. 8G). The second wafer 160 may now be etched to expose the alignment mark 151*m* on top of the first wafer 150 (FIG. 8H). The 0.2 μm siliconoxide layer 164 of the second wafer 160 may then be etched FIG. 8I, after which polysilicon 164*ps* may be deposited in etch holes 164*h* therein (FIG. 83). After this, the second wafer 160 can be etched such that the contacts in the first wafer 150 are exposed again and be provided with an electrically conductive layer. For example a metal or an alloy of metals, e.g. AlCu may be deposited at these exposed locations, to create the bondpads 22 (FIG. 8K). Next, via DRIE etching the pattern of the comb drive and the torsion beams to be formed may also be etched in the second silicon layer (FIG. 8L), in this embodiment having a thickness of 27 micrometer. The siliconoxide layer 164 in the area assigned to the comb drive may now be removed via etching (FIG. 8M).

When a DSOI wafer is used instead of wafers 150 and 160, the start assembly is analogous to the one shown in FIG. 8E, but without any etched structures. First, side 152 can be protected with thermal oxidation, and marker 152*m* can be etched. Next, the top silicon layer can be grounded back to the top siliconoxide layer 164, analogously as shown FIG. 8F. Further, analogous to what is shown in FIG. 8G, after turning of the wafer, the backside 152 can be etched. Layer 164 and 165 can be etched to create alignment mark 151*m*. Next, the siliconoxide layer 164 can be etched, analogous to FIG. 8I, and analogous to FIG. 8J polysilicon 164*ps* may be deposited in etch holes 164*h* formed in the etching step of FIG. 8I. Next, the top silicon layer 160 can be etched to expose the locations 160*e*, as shown in dashed lines in FIG. 8F. After exposure, bondpads 156 can be created in the layers below, analogously as shown in and described with reference to FIG. 8C and FIG. 8D, via partial-oxygen-etch holes. The created etch holes may be provided with an electrical conductive layer. For example a metal or metal alloy, e.g. AlCu may be deposited at these exposed locations 160*e* to create the bondpads 22, as analogously shown in and described with reference to FIG. 8K. Next, via DRIE etching the pattern of the comb drives end torsion beams can be etched, possibly in two or more steps with different etching masks to provide all the detail, in the top two silicon wafers, analogous to FIG. 8L and FIG. 8C. The siliconoxide layer 164 in the area assigned to the comb drive may now be removed via etching, analogous to FIG. 8M. The manufacturing process may then proceed with the step below described with reference to FIG. 8N, regardless whether the process started with separate SOI wafers 150 and 160, or one combined DSOI wafer.

In this subsequent step, thermal oxidation can be applied to outer surfaces 171, 172 of the third wafer 170 (FIG. 8N). Alignment marker 172*m* can be etched. As further shown in FIG. 8N, one of these surface 171 can be etched to create deposition locations 171*d* for deposition of electric contacts 171*c*. In the embodiment shown these contacts 171*c* are obtained by deposition of a gold layer in these locations (FIG. 8O).

Next, a pattern of the main part of the rotor 14RB and the rotor support 14RS may be etched in the third wafer 170 with DRIE etching (FIG. 8P). Subsequently, the third wafer 170 can be mechanically and electrically connected to the assembly of the first wafer 150 and the second wafer 160 via an eutectic bond (FIG. 8Q) with the exposed surface of the second wafer 160. The semi-finished product comprising the first, second and third wafer may now be released at the side of the first wafer, and may be turned to etch the second silicon layer 155 of the first wafer with DRIE etching to open up the area defined for the comb drive and the torsion beams (FIG. 8R). Next, the intermediate insulator layer 154 of siliconoxide may be etched in the same area at the base side of the comb drive structure, to fully open up the comb drives (FIG. 8S). The MEMS assembly can now be turned around, such that the third wafer 170 is at the top side, after which via DRIE etching the third wafer 170 may be cut free (FIG. 8T). A reflective layer, for example an Al or Au layer having a thickness of some tens of nm, e.g. 50 nm may then be deposited and patterned on top of the third wafer surface to form the mirror surface 14MS (FIG. 8U).

Figure 9:
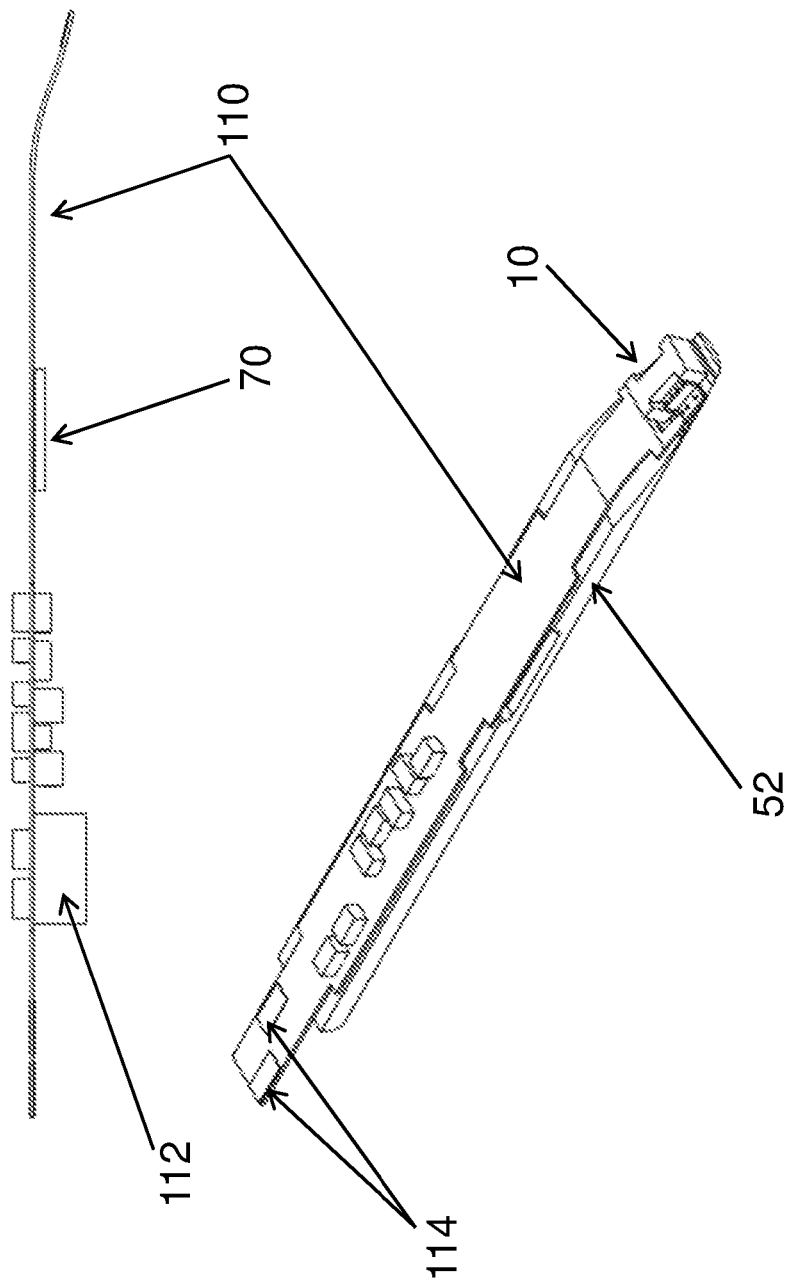
FIG. 9 schematically shows a possible placement of the MEMS mirror, driver, and other components on a flexible printed circuit board in the probe.
Figure 10:
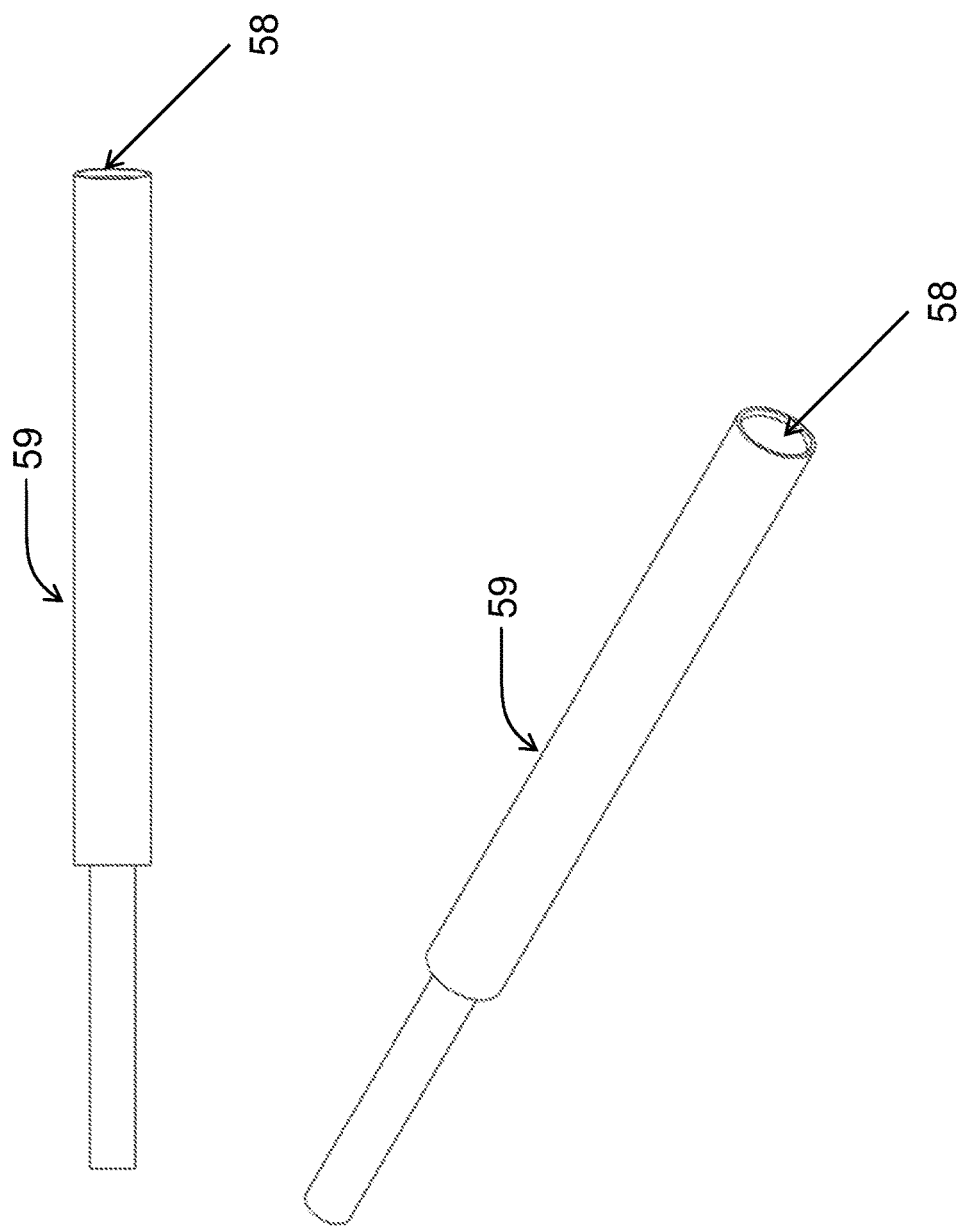
FIG. 10 schematically shows a possible way to manufacture a catheter tube around the probe tip.

The top part 53 and carrier part 52 of the housing can be 3D printed in medical grade plastic. Passive electric components including resistors, capacitors and an inductor for example may be connected to both mutually opposite faces of a flexible printed circuit board 110 (FIG. 9). An ASIC 70, serving as the driver for the MEMS 10, can be ground back to a naked die, and be stud-bumped. This stud-bumped ASIC can then be connected to one side of the flexible printed circuit board. Electrically conductive wires can be soldered to pads 114 on the back side of the flexible printed circuit board to enable receiving and sending of signals from and to the ASIC 70, e.g. a signal that provides the angular position of the mirror. The flexible printed circuit board can be glued to the carrier part 52, in such a way that an inductor 112 and the ASIC are on the surface of the flexible printed circuit board that faces the carrier part. The MEMS mirror 10 can now be glued to the end portion 34 of the flexible printed circuit board 110. The assembly of the carrier part 52 and the flexible printed circuit board can be clamped inside an assembly holder, such that wire bonding of the six bond pads 22 of the MEMS mirror can take place. The top part 53 can now be glued in place on top of the assembly of the carrier part 52 and the printed circuit board 110, after which the optical fibre assembly can be placed on top of this support in the groove that is made for that purpose. Next, the fibre assembly can be aligned with the MEMS mirror. To turn this probe into a watertight catheter, the viewing window 58 can be glued to the front side of the top support, under an angle of 8° to avoid static back reflection. Next, a heat shrink tube 59 will be pulled around the support structure, which can be at least 1 cm longer than the support structure itself (FIG. 10), extending at the first (optical interface) side of the probe. At the second (viewing window) side the heat shrink tube will be shrunk around the edges of the window 58. A longer heat shrink tube can be pulled around the wires, and over the 1 cm extension of the other heat shrink tube, where both tubes can be glued together. At the opposite end of this long tube a split can be made such that the tube is split in mutually separate tubes, one for the optical fibre and one for electrical conductors to the probe. Both tubes end with a corresponding connector.

The invention claimed is:

1. A MEMS mirror having:
    a stator,
    a rotor, having a rotor support and a rotor body, said rotor support having a first end facing the stator and an opposite, second end that is fixed to a first face of the rotor body, said rotor body having a mirror surface at a second face oppostie the first face,
       wherein said rotor support spaces the rotor body from the stator over a range of rotation of the rotor with respect to the stator, and
    a pair of comb elements that are manually interdigitated in a neutral state of the rotor, said pair of comb elements including:
       a first comb element fixed to the stator and defining a reference plane, having a surface that divides a first side of the reference plane from an opposite, second side of the reference plane, and
       a second comb element fixed to the first end of the rotor support,
    wherein the rotor support is coupled at mutually opposite sides of the first end via respective torsion beams to the stator, wherein the respective torsion beams extend along a rotation axis in the reference plane to allow the rotor to rotate over said range of rotation along the rotation axis, and
    the stator and the rotor support are at, respectively, said first and second sides of the reference plane.

2. The MEMS mirror according to claim 1, wherein at least one of the following applies: (1) a size of the mirror surface in a direction transverse to the rotation axis is at least 90% of a size of the stator in said transverse direction, or (2)

a distance between mutually opposed edges of the mirror surface in that direction is at least 200 micrometers greater than a distance between mutually opposed edges of the stator in said transverse direction.

3. The MEMS mirror according to claim 2, wherein the rotor has peripheral portions that extend beyond the stator in said transverse direction and that are aligned with said reference plane.

4. The MEMS mirror according to claim 3, wherein a respective end of each peripheral portion has a respective extension portion that is spaced apart from a respective side face of the stator.

5. The MEMS mirror according to claim 1, further comprising at least one further pair of comb elements including a third comb element fixed to the stator and a fourth comb element fixed to a peripheral portion of the rotor.

6. The MEMS mirror according to claim 1, wherein the torsion beams have a T-shaped cross-section in a plane transverse to the rotation axis.

7. The MEMS mirror according to claim 1, wherein silicon vias electrically connect the pair of comb elements to respective electric contacts at a surface of the stator facing away from the mirror surface.

8. The MEMS mirror according to claim 7, wherein the size of the mirror surface in a direction of the rotation axis is at least 90% of the size of the stator in said direction of the rotation axis.

9. A forward looking MEMS based optical coherence tomography (OCT) probe, comprising:
 an elongate probe having at a first end a probe interface for an optic fibre, and at a second opposite end a viewing window, and
 a probe housing that includes the MEMS mirror of claim 1 for sweeping a light beam through the viewing window and for reflecting light received through the viewing window towards the probe interface, wherein the rotation axis of the MEMS mirror extends transverse to a longitudinal axis of said probe housing extending from said first end to said second opposite end.

10. The OCT probe according to claim 9, wherein the housing further includes a driver having an output to provide a drive signal to an actuator.

11. The OCT probe according to claim 10, wherein the driver is further provided at least with a feedback input to receive a feedback signal indicative for a rotational state of the rotor, the driver being configured to provide the drive signal at the output based on said feedback signal.

12. The OCT probe according to claim 11, wherein the feedback signal is a zero-crossing, synchronisation, or trigger signal.

13. The OCT probe according to claim 10, wherein the first comb element fixed to the stator, the second comb element fixed to the first end of the rotor support, a third comb element fixed to the stator, and a fourth comb element fixed to a peripheral portion of the rotor, each include:
 a first and a second, mutually insulated, comb layer of an electrically conducting material, wherein:
 the first comb layer faces the mirror surface, and the second comb layer faces away from the mirror surface,
 the first and the second comb layer respectively form a first and a second electric pole in each of the comb elements,
 the first electric poles of each of the first and third comb elements fixed to the rotor are electrically interconnected with each other, and are electrically connected to the output of the driver,
 at least one of the first and the second electric pole of the second and fourth comb elements fixed to the stator are coupled to a respective feedback input of the driver, and
 the second and fourth comb elements fixed to the stator are arranged at mutually opposite sides of the rotation axis.

14. The OCT probe according to claim 9, having an operational state wherein the MEMS mirror operates in a resonance mode with a resonance frequency between 200 Hz and 4000 Hz.

15. The OCT probe according to claim 9, wherein the probe comprises a SMF (single mode fibre), a spacer, a GRIN lens bound by tilted faces with respect to said longitudinal axis, a prism, the MEMS mirror, and the viewing window.

16. The OCT probe according to claim 9, wherein:
 the probe housing accommodates a carrier having:
 a main portion extending in a direction substantially coinciding with said longitudinal axis of the housing, and
 an end portion facing the viewing window,
 wherein:
 the main portion carries a driver and the end portion carries the MEMS mirror, and
 the carrier at a side carrying the MEMS mirror is tilted with respect to said longitudinal axis.

17. The OCT probe according to claim 16, wherein the end portion of the carrier is provided with recesses facing peripheral portions of the rotor, or wherein the stator of the MEMS mirror is arranged on a pedestal on the end portion of the carrier.

18. A forward looking MEMS based OCT system, comprising the OCT probe according to claim 9, and further including:
 a coherent light source configured to generate a coherent light beam;
 a beam splitter/merger to split the coherent light beam into a reference beam and a sense beam;
 a reference unit to receive and reflect the reference beam; and
 wherein the probe interface of the OCT probe is to configured receive the sense beam and the beam splitter/merger is configured to receive the light reflected from the sample, received through the viewing window, and reflected by the MEMS mirror, and further configured to receive the reflected reference beam and to merge the beams received from the reference unit and the probe;
 a detector to generate a detection signal indicative for the merged beam;
 a processing unit to process the detection signal.

19. A method of manufacturing the MEMS mirror according to claim 1, wherein
 the first comb element fixed to the stator and the second comb element fixed to the first end of the rotor support each have at least a first and a second mutually insulated, electrically conductive layer,
 the method comprising:
 using a first wafer having a first silicon device layer to form the second electrically conductive layers of the first and second comb elements and at least the stator;
 using a second wafer having a second silicon device layer to form the first electrically conductive layers of the first and second comb elements, and
 using a third wafer to form the rotor.

20. A method of manufacturing the MEMS mirror according to claim 1, wherein the first comb element fixed to the stator and the second comb element fixed to the first end of the rotor support each have at least a first and a second mutually insulated, electrically conductive layer, the method comprising:

using a first wafer having at least a first and a second silicon device layers to form the first and the second electrically conductive layers of the first and second comb elements and at least the stator and using a second wafer to form the rotor.

* * * * *